United States Patent
Kobayashi et al.

(10) Patent No.: US 12,078,524 B2
(45) Date of Patent: Sep. 3, 2024

(54) WEIGHT MEASUREMENT DEVICE

(71) Applicant: Tanita Corporation, Tokyo (JP)

(72) Inventors: Kotaku Kobayashi, Tokyo (JP); Seiya Ichihara, Tokyo (JP); Hiroyuki Yamada, Daisen (JP)

(73) Assignee: TANITA CORPORATION, Tokyo (JP)

( * ) Notice: Subject to any disclaimer, the term of this patent is extended or adjusted under 35 U.S.C. 154(b) by 545 days.

(21) Appl. No.: 17/472,547

(22) Filed: Sep. 10, 2021

(65) Prior Publication Data

US 2022/0003592 A1 Jan. 6, 2022

Related U.S. Application Data

(63) Continuation-in-part of application No. PCT/JP2020/008951, filed on Mar. 3, 2020.

(30) Foreign Application Priority Data

Mar. 13, 2019 (JP) ................. 2019-046250

(51) Int. Cl.
*G01G 3/14* (2006.01)
*A61B 5/05* (2021.01)
(Continued)

(52) U.S. Cl.
CPC ............ *G01G 3/14* (2013.01); *G01G 19/44* (2013.01); *G01G 21/22* (2013.01); *A61B 5/0537* (2013.01)

(58) Field of Classification Search
CPC ........ A61B 5/0537; G01G 3/14; G01G 19/44; G01G 21/22
See application file for complete search history.

(56) References Cited

U.S. PATENT DOCUMENTS 9,494,459 B2 11/2016 Oneid
2008/0271931 A1 11/2008 Weichao
(Continued)

FOREIGN PATENT DOCUMENTS

JP  2003-149038 A  5/2003
JP  2012-145389 A  8/2012
(Continued)

OTHER PUBLICATIONS

Extended European Search Report issued in corresponding European Patent Application No. 20770516.1 dated Sep. 1, 2022.
(Continued)

*Primary Examiner* — Randy W Gibson
(74) *Attorney, Agent, or Firm* — Morgan, Lewis & Bockius LLP

(57) ABSTRACT

A weight measurement device comprises: an upper surface cover on which a measurement target is placed; a load cell to detect weight of the measurement target placed on the upper surface cover; a bridge to support the load cell; a receiving member to receive the weight of the measurement target placed on the upper surface cover; and a bottom surface cover provided on a lower surface side of the receiving member, and further comprises a sliding part provided between the lower surface of the receiving member and an upper surface of the bottom surface cover to enable the receiving member to move in a horizontal direction relative to the bottom cover. The bridge comprises a pivot which is a fulcrum to make it possible to change inclination of the bridge relative to the bottom surface cover and is in contact with an upper surface of the receiving member.

20 Claims, 18 Drawing Sheets

(51) Int. Cl.
    *G01G 19/44*     (2006.01)
    *G01G 21/22*     (2006.01)
    *A61B 5/0537*    (2021.01)

(56)           References Cited

U.S. PATENT DOCUMENTS

| | | | | |
|---|---|---|---|---|
| 2009/0183928 | A1* | 7/2009 | Oseko | G01G 23/3728 |
| | | | | 177/211 |
| 2014/0291042 | A1* | 10/2014 | Tsutaya | G01L 1/2206 |
| | | | | 73/862.632 |
| 2015/0101870 | A1 | 4/2015 | Gough et al. | |
| 2021/0262852 | A1* | 8/2021 | Xiang | G01G 19/62 |

FOREIGN PATENT DOCUMENTS

| | | |
|---|---|---|
| JP | 2014-066572 A | 4/2014 |
| JP | 2014-190780 A | 10/2014 |

OTHER PUBLICATIONS

International Search Report issued in related International Patent Application No. PCT/JP2020/008951 Apr. 4, 2020.

* cited by examiner

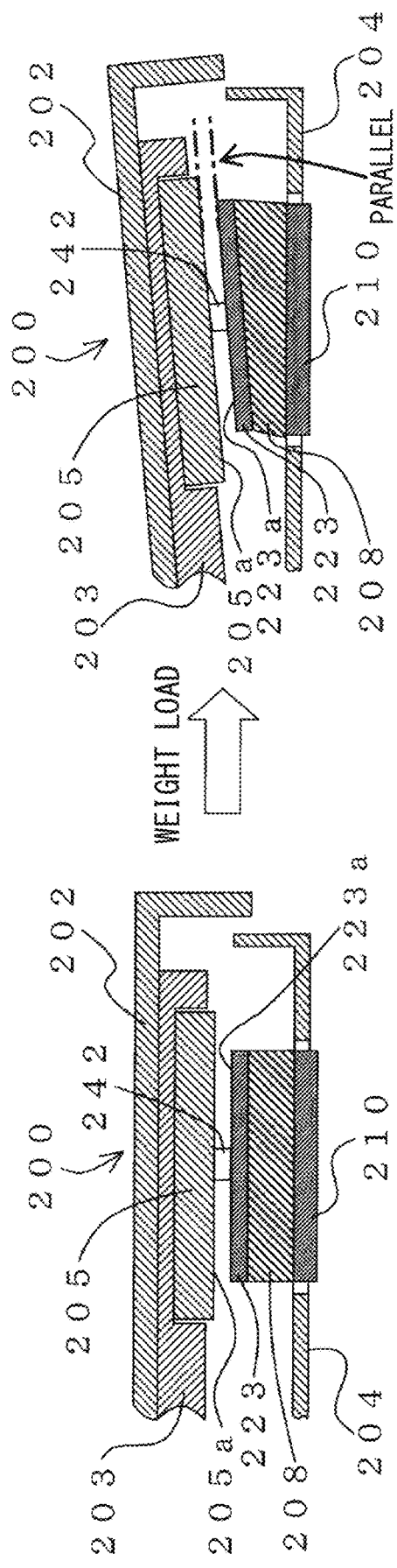

WEIGHT MEASUREMENT DEVICE

TECHNICAL FIELD

The present invention relates to a weight measurement device for measuring the weight of a measurement target.

BACKGROUND ART

Conventionally, there are known weight measurement devices for measuring the weight of a measurement target such as a human body. Generally, a weight measurement device has at least one load cell (normally four in the case of a weight scale) to which the weight of a measurement target is transferred. A load cell has a strain generating body to deform when the weight of the measurement target is transferred thereto, and a strain gauge for generating a signal corresponding to the deformation of the strain generating body. Based on the signal output from the strain gauge described above, a processing circuitry on a board calculates the weight of the measurement target.

In conventional weight measurement devices, there is a weight measurement device 200 as shown in FIG. 19 which is designed so that when a measurement target is placed on an upper surface cover 202 while a rubber 208 is sandwiched between a bridge 223 and a leg 210, a weight (upward force) from the leg 210 is transferred to (movable arm parts of) a load cell 205 through the rubber 208 and the bridge 223 (refer for example to Patent Document 1). Note that a member 242 in FIG. 19 is a boss (a member equivalent to the boss 42 in FIG. 2 described later) integrally formed with the bride 223, and serves as a spacer to keep the distance between a lower surface 205*a* of the load cell 205 and an upper surface 223*a* of the bridge 223. In this weight measurement device 200, as shown on the right side of FIG. 19, when the upper surface cover 202 and a housing 203 are loaded with the weight of the measurement target, the load cell 205 inclines as the upper surface cover 202 and the housing 203 deflect due to the weight. Corresponding to this inclination, the rubber 208 is a little compressed while deforming in a horizontal direction, causing the upper surface of the rubber 208 to incline, whereby the bridge 223 inclines corresponding to the inclination of the load cell 205, making it possible to keep the upper surface 223*a* of the bridge 223 to be in parallel to the lower surface 205*a* of the load cell 205.

According to this weight measurement device 200, as described above, the upper surface 223*a* of the bridge 223 can be kept in parallel to the lower surface 205*a* of the load cell 205, and therefore, upward force in the vertical direction can be stably applied to (the movable arm parts of) the load cell 205 from the bridge 223. Therefore, regardless of the manner of deflection of the upper surface cover 202 and the housing 203, an accurate output from (the strain gauge of) the load cell 205 can be obtained, thus making it possible to accurately measure the weight of the measurement target.

PRIOR ART DOCUMENTS

Patent Documents

[Patent Document 1] Japanese Laid-open Patent Publication 2014-66572

SUMMARY OF THE INVENTION

Problem to be Solved by the Invention

However, in order to allow that the rubber 208 is sandwiched between the bridge 223 and the leg 210, and this rubber 208 is used to keep the upper surface 223*a* of the bridge 223 to be in parallel to the lower surface 205*a* of the load cell 205 as in the conventional weight measurement device 200 described above, the rubber 208 is required to be some sufficiently thick rubber (for example, 5 mm), causing the problem that it is not possible to achieve reduction in the thickness of the entire device.

An object of the present invention is to solve the problems described above and to provide a weight measurement device which can obtain an accurate output from a load cell, and can accurately measure the weight of the measurement target, regardless of the manner of deflection of an upper surface cover and so on, and which can achieve reduction in the thickness of the entire device.

Means to Solve the Problem

In order to solve the above problem, a weight measurement device according to the present invention comprises: an upper surface cover on which a measurement target is placed; a load cell to detect weight of the measurement target placed on the upper surface cover; a bridge to support the load cell; a receiving member to receive the weight of the measurement target placed on the upper surface cover; and a bottom surface cover provided on a lower surface side of the receiving member, wherein the weight measurement device further comprises a sliding part provided between the lower surface of the receiving member and an upper surface of the bottom surface cover to enable the receiving member to move in a horizontal direction relative to the bottom cover, and wherein the bridge comprises a pivot which is a fulcrum to make it possible to change inclination of the bridge relative to the bottom surface cover and is in contact with an upper surface of the receiving member.

In this weight measurement device, it is preferable that friction coefficient of the sliding part is set to satisfy the relationship that when the upper surface cover deflects due to the weight of the measurement target placed on the upper surface cover, friction force generated between the receiving member and the bottom surface cover is smaller than friction force generated between the pivot and the receiving member.

In this weight measurement device, the sliding part can be a sheet made of resin pasted on at least one of the lower surface of the receiving member and the upper surface of the bottom surface cover.

In this weight measurement device, the sheet made of resin can be a sheet made of fluorocarbon resin.

In this weight measurement device, the sliding part can be resin coated on at least one of the lower surface of the receiving member and the upper surface of the bottom surface cover.

In this weight measurement device, the coated resin can be fluorocarbon resin.

In this weight measurement device, the sliding part can be at least one of the lower surface of the receiving member and the upper surface of the bottom surface cover having been subjected to plating treatment.

In this weight measurement device, the receiving member can comprise: a plate-shaped part in contact with the pivot; an elastic part provided on an outer periphery of the plate-shaped part; and an outer frame part provided on an outer periphery of the elastic part, wherein only the outer frame part can be attached to the bottom surface cover without attaching the plate-shaped part and the elastic part to the bottom surface cover.

In this weight measurement device, it can further comprise a leaf spring to attach the bridge to the bottom surface cover side, wherein the leaf spring can have a peripheral part fixed to the bottom surface cover, and is formed to be elastically deformable.

In this weight measurement device, the leaf spring can be connected to the upper surface cover side, wherein the weight measurement device can further comprise a separation prevention member to prevent the bottom surface cover from being separated from the upper surface cover by a given distance or more, and wherein the given distance can be a distance to prevent the leaf spring fixed to the bottom surface cover side from being stretched to its limit.

In this weight measurement device, it can further comprise a reinforcement cover connected to the upper surface cover, wherein the reinforcement cover can comprise an upper surface cover made of metal, a bottom surface cover made of metal, and a resin layer provided between the upper surface cover made of metal and the bottom surface cover made of metal, wherein many fine recessed parts can be formed in a lower surface of the upper surface cover made of metal and an upper surface of the bottom surface cover made of metal, and wherein resin of the resin layer can be filled into the many fine recessed parts so as to bond the upper surface cover made of metal, the resin layer and the bottom surface cover made of metal.

Effects of the Invention

According to the present invention, even if the pivot becomes unable to move in a horizontal direction relative to the receiving member due to the friction force generated between the pivot of the bridge and the upper surface of the receiving member when the upper surface cover deflects due to the weight of a measurement target, it is possible to move the receiving member in a horizontal direction relative to the bottom surface cover due to the function of the sliding part provided between the lower surface of the receiving member and the upper surface of the bottom surface cover. Therefore, the inclination of the bridge relative to the bottom surface cover can be changed by moving the pivot in a horizontal direction relative to the bottom surface cover. Thus, when the upper surface cover deflects due to the weight of the measurement target, it is possible to keep the inclination between the upper surface of the bridge and the lower surface of the load cell (for example, to keep the upper surface of the bridge to be in parallel to the lower surface of the load cell) in the state when the upper surface cover does not deflect, making it possible to stably apply an upward force from the bridge in a vertical direction to the lower surface of the load cell. Therefore, regardless of the manner of deflection of the upper surface cover, an accurate output from the load cell can be obtained, making it possible to accurately measure the weight of the measurement target. In addition, in contrast to the weight measurement device shown in Patent Document 1, a thick rubber is not required to be placed under the bridge, therefore making it possible to achieve the reduction in thickness of the entire device.

BRIEF DESCRIPTION OF THE DRAWINGS

FIG. 19 Explanatory view of the configuration around a load cell according to an example of a conventional weight measurement device.

DESCRIPTION OF EMBODIMENTS

Hereinafter, an exemplary embodiment of the present invention will be described with reference to the drawings. The present embodiment describes an example in which the weight measurement device of the present invention is a body composition meter.

Figure 1:
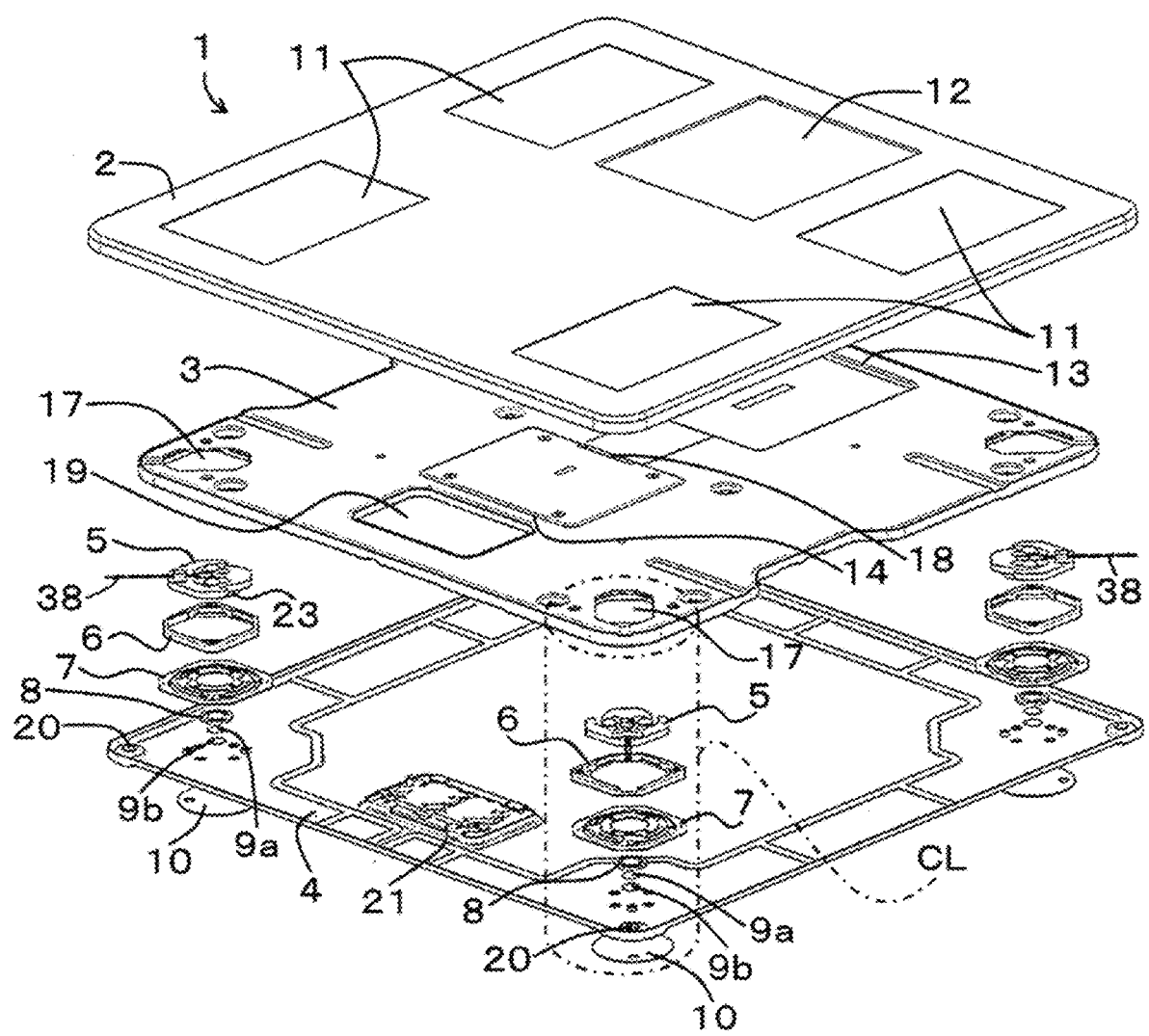
FIG. 1 Exploded perspective view of a body composition meter according to an exemplary embodiment of the present invention.

FIG. 1 is an exploded perspective view of the entire body composition meter according to the present embodiment. The body composition meter 1 has a function to measure the weight of a subject, and a function to measure the body composition of the subject such as body fat rate, amount of muscle, estimated amount of bone, visceral fat level, amount of basal metabolism, body water rate and so on. As shown in FIG. 1, the body composition meter 1 comprises, as its housing, a resin cover 2 ("upper surface cover" in the claims) on which a subject is placed, a reinforcement cover 3 formed by combining a metal and a resin, and a bottom cover 4 ("bottom surface cover" in the claims). Although details of the reinforcement cover 3 will be described later, this reinforcement cover 3 is a member to increase the strength of the resin cover 2 by being bonded to the resin cover 2. The bottom cover 4 is formed by a material made of metal such as steel plate. Further, as shown in FIG. 1, the body composition meter 1 comprises legs 10 placed on four corners of the bottom surface of the bottom cover 4.

As shown in FIG. 1, the body composition meter 1 comprises four electrodes 11 on an upper surface of the resin cover 2 to measure a bioelectrical impedance of a subject. These electrodes 11 include left and right current supply electrodes to apply current to the soles of both left and right feet of the subject, and left and right voltage detection electrodes to detect a voltage corresponding to a potential difference generated between the soles of both feet of the subject due to the current application from the current supply electrodes. Further, the body composition meter 1 comprises a display unit. This display unit is formed by a display window 12 provided in the upper surface of the resin cover 2, and a not shown LCD module attached to a recessed part 13 provided on an upper surface of the reinforcement cover 3. The weight, body composition and so on of the subject are displayed on this display unit.

Further, a not shown board is attached to a recessed part provided on a back surface side of a projected part 14 of the reinforcement cover 3. This board comprises a processing circuitry to perform a measurement process of the weight of the subject, a measurement process on various body compositions of the subject and other processes, and so on. The LCD module placed on the upper surface side of the reinforcement cover 3 described above is connected to the board placed on the bottom surface side of the reinforcement cover 3. More specifically, a flexible cable integrally provided with the LCD module is passed through a through-hole 18 formed in a central part of the reinforcement cover 3, and an end of the flexible cable is connected to the board on the bottom surface side of the reinforcement cover 3. Further, holes 17 are formed in the reinforcement cover 3 having a substantially rectangular shape at positions corresponding to its four corners in order to secure space to allow the movable arm parts 34 (refer to FIG. 2 and so on) of the load cells 5 to move upward when the subject steps on the resin cover 2. In addition, a hole 19 is formed in the reinforcement cover 3 in order to secure space for a battery box 21 provided on the bottom cover 4.

Figure 2:
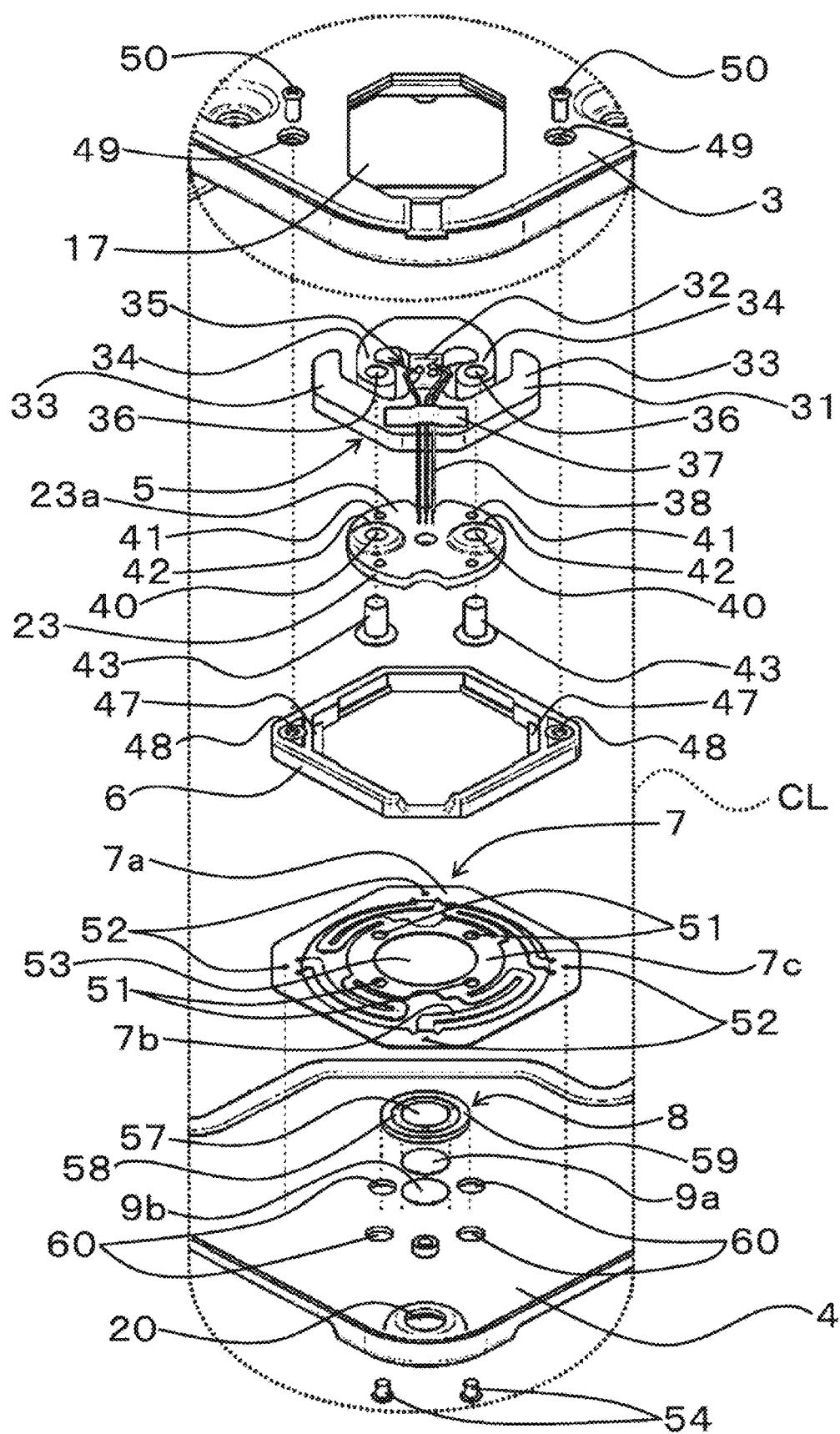
FIG. 2 Detailed exploded view of members of the body composition meter around a load cell.

Next, referring to FIG. 2 in addition to FIG. 1 described above, members of the body composition meter 1 around the load cell 5 will be described. FIG. 2 is a detailed exploded view of members of the body composition meter 1 around the load cell 5, showing an enlarged view of a part corresponding to a column-shaped area CL shown by a dot-dashed line in FIG. 1. Note that FIG. 1 shows the load cells 5 in a state where they are fixed to the bridge 23, while FIG. 2 shows the load cell 5 before it is fixed to the bridge 23.

As shown in FIG. 2, the body composition meter 1 comprises around the load cell 5: the bridge 23 which is a member to transfer weight to the load cell 5 and supports the load cell 5 and has a pivot 62 (refer to FIG. 4); a sensor holder 6 which is a member to hold the load cell 5; a leaf spring 7 for attaching the bridge 23 to the bottom cover 4; a receiving member 8 to receive (receive and hold) the weight from the subject on the resin cover 2; and low friction sheets 9a, 9b. Although details will be described later, the leaf spring 7 has a peripheral part fixed to the bottom cover 4, and is formed to be elastically deformable. The low friction sheets 9a, 9b are sheets made of fluorocarbon resin, and correspond to the sliding part in the claims. The low friction sheets 9a, 9b have a static friction coefficient of, for example, 0.3 or lower. Further, the low friction sheets 9a, 9b have a thickness of, for example, 0.05 mm to 0.2 mm per sheet.

Figure 3:
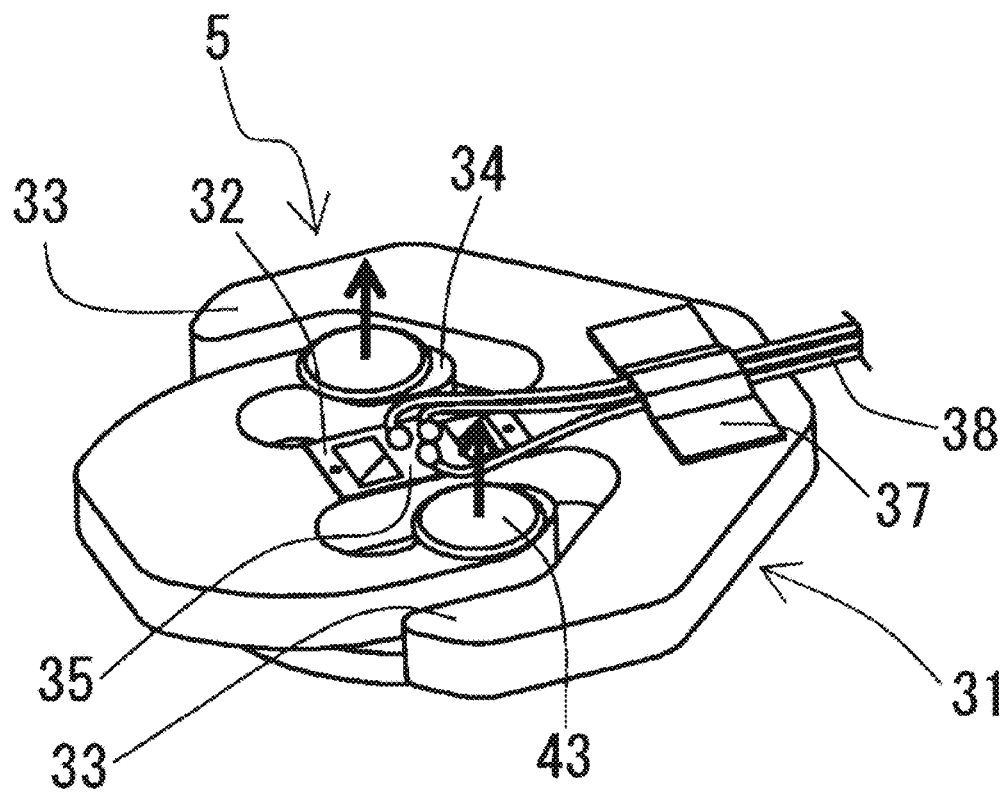
FIG. 3 Perspective view of the load cell of the body composition meter as seen from diagonally upward.
Figure 4:
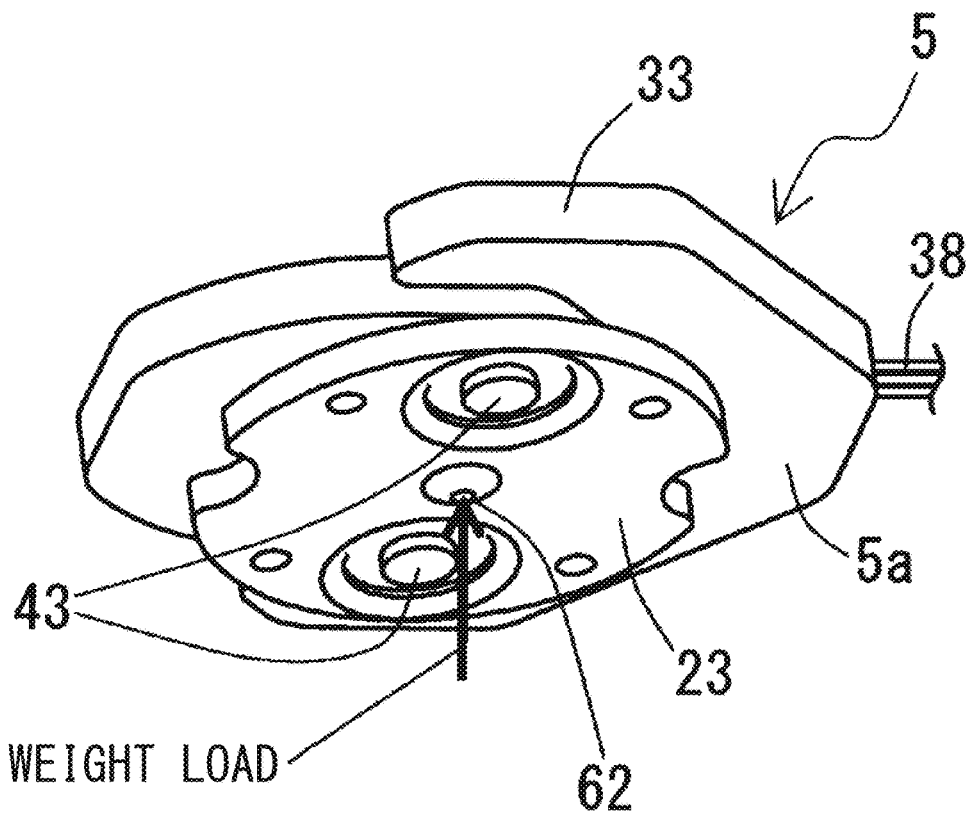
FIG. 4 Perspective view of the load cell as seen from diagonally downward.
Figure 5:
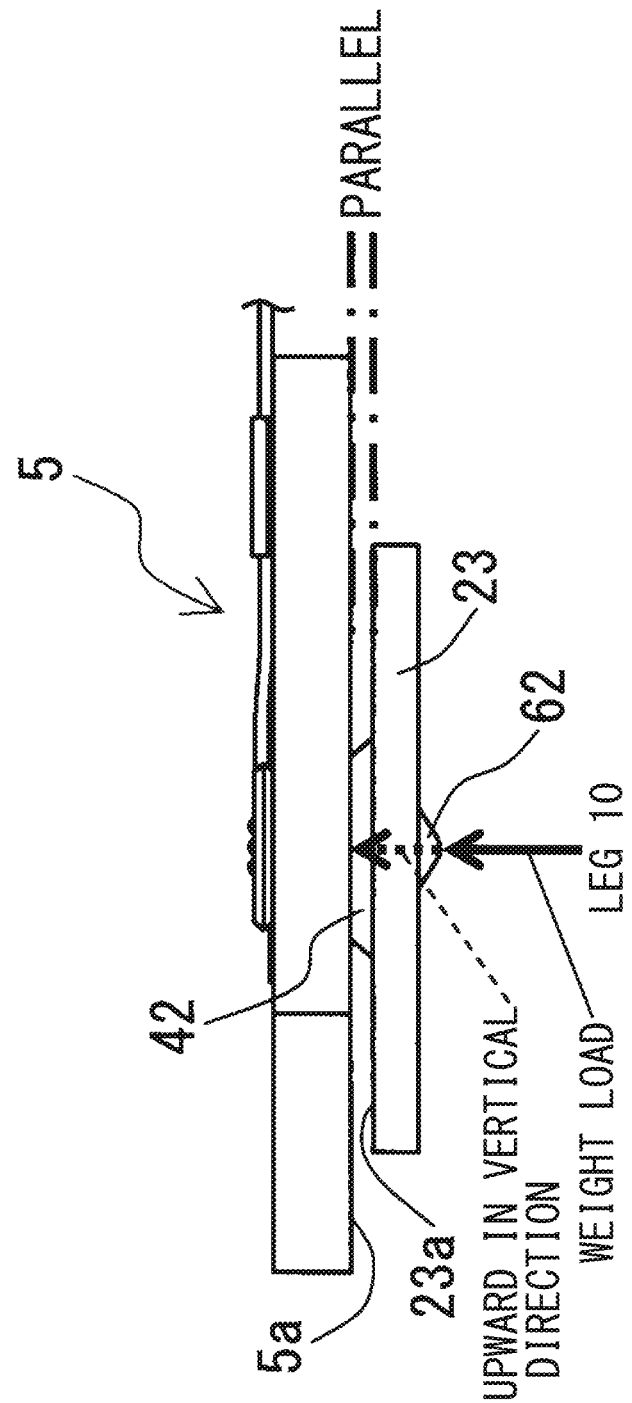
FIG. 5 Side view of the load cell.

Next, referring to FIG. 3 to FIG. 5 in addition to FIG. 2 described above, the structure of the load cell 5 will be described. FIG. 3 and FIG. 4 are perspective views of the load cell 5 as seen from diagonally upward and diagonally downward, respectively, while FIG. 5 is a side view of the load cell 5. FIG. 3 to FIG. 5 show the load cell 5 in the state where it is fixed to the bridge 23. The load cell 5 has a strain generating body 31 to deform when the weight of a subject on the resin cover 2 is transferred thereto, and a strain gauge 32 to generate a signal corresponding to the deformation of the strain generating body 31, and detects the weight of the subject. The strain generating body 31 is a single member having a line-symmetric shape and a uniform thickness, and comprises: two fixed arm parts 33 fixed to the reinforcement cover 3; two movable arm parts 34 to receive the weight from the leg 10 through the receiving member 8 and the bridge 23; a strain generating part 35 to generate a strain when the movable arm parts 34 receive the weight; and two through-holes 36 (refer to FIG. 2). Further, a cable 38 of the strain gauge 32 is attached in contact to the strain generating body 31 with a tape 37. This tape 37 serves to bundle the cable 38 of the strain gauge 32.

As shown in FIG. 4 and FIG. 5, the bridge 23 comprises on the lower surface at a central part thereof a pivot 62 having a shape formed by turning upside down a cone with a hemisphere-shaped top. This pivot 62 is a fulcrum to make it possible to change the inclination of the bridge 23 relative to the bottom cover 4, and is arranged to be in contact with an upper surface of the receiving member 8 in the body composition meter 1 after assembly. The pivot 62 has a height of, for example, 0.8 mm. Further, as shown in FIG. 2, the bridge 23 has two through-holes 40 at positions corresponding to the two through-holes 36 of the load cell 5 side. As shown in FIG. 2 and FIG. 5, truncated cone-shaped bosses 42 are provided around the through-holes 40 on an upper surface 23a of the bridge 23. Thus, as shown in FIG. 5, at the upper surface 23a of the bridge 23, only the upper surfaces of the two bosses 42 are brought in contact with the lower surface of the load cell 5 in the state where load cell 5 is fixed to the bridge 23. In other words, the bosses 42 of the bridge 32 serve as spacers to keep the distance between the lower surface 5a of the load cell 5 and the upper surface 23a of the bridge 23. Further, as shown in FIG. 2, the bridge 23 has at four peripheral locations thereof threaded screw holes 41 in which small screws 54 for fixing with the leaf spring 7 are screwed.

Next, a method of attaching the load cell 5, the bridge 23 and the sensor holder 6 to the reinforcement cover 3 will be described. First, the fixing of the load cell 5 to the bridge 23 is done with rivets 43 shown in FIG. 2 to FIG. 4. More specifically, as shown by dashed lines in FIG. 2, two rivets 43 are passed from downward through the through-holes 40 of the bridge 23 side and two through-holes 36 of the load cell 5 side, and then upper ends of the rivets 43 are crimped so as to fix the load cell 5 to the bridge 23. Then, fixed arm parts 33 of the load cell 5 in a state where it is fixed to the bridge 23 are fitted into a frame 47 of the sensor holder 6, and thereafter, the sensor holder 6 with the load cell 5 fitted therein is attached to a frame 73 (refer to FIG. 7) provided on the back surface side of the reinforcement cover 3. Further, as shown by dashed lines in FIG. 2, small screws 50 are screwed in screw holes 49 of the reinforcement cover 3 and screw holes 48 of the sensor holder 6 so as to fix (screw) the reinforcement cover 3 to the sensor holder 6, whereby the load cell 5, the bridge 23 and the sensor holder 6 are attached to the reinforcement cover 3.

Figure 6:
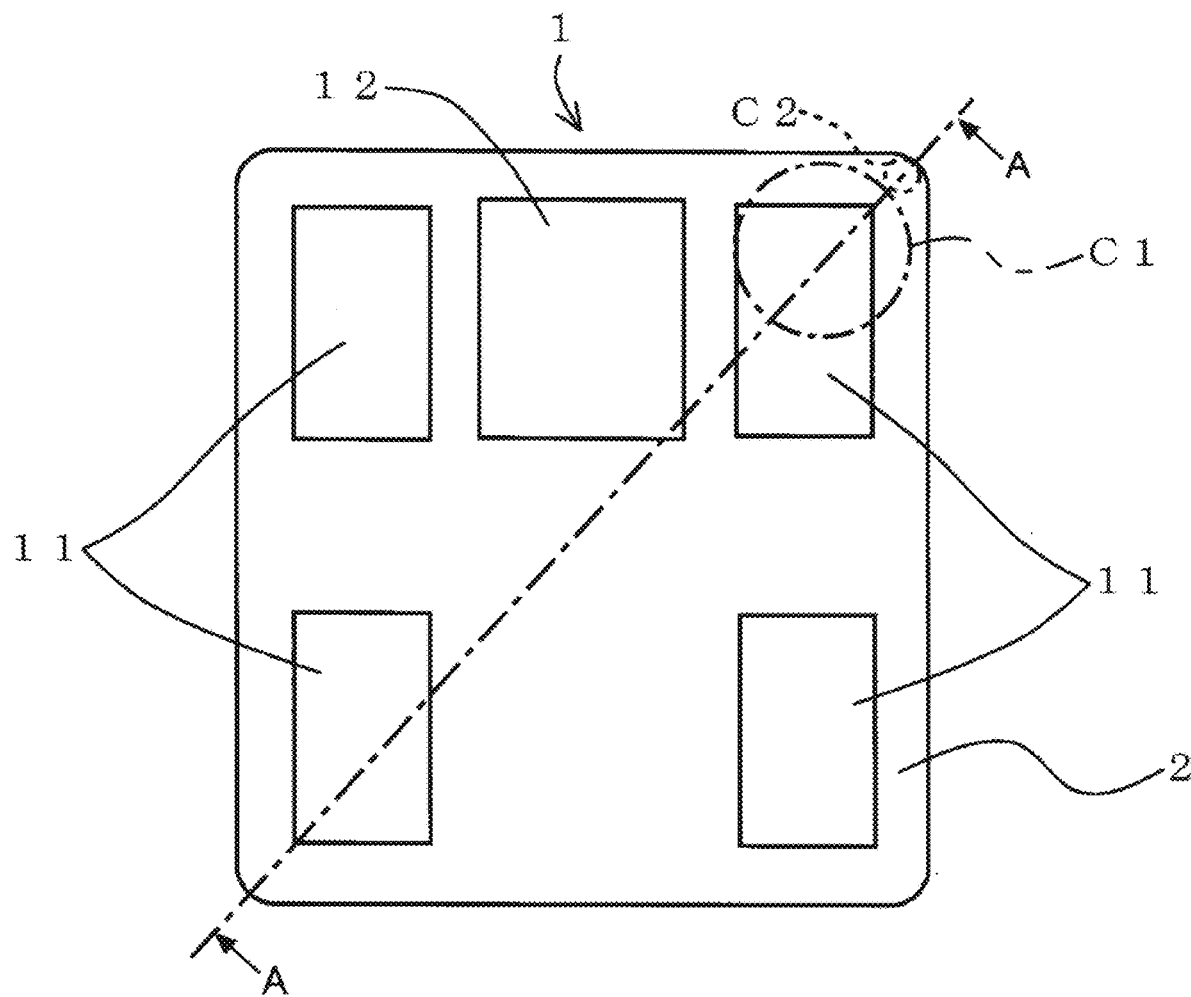
FIG. 6 Top plan view of the body composition meter.
Figure 7:
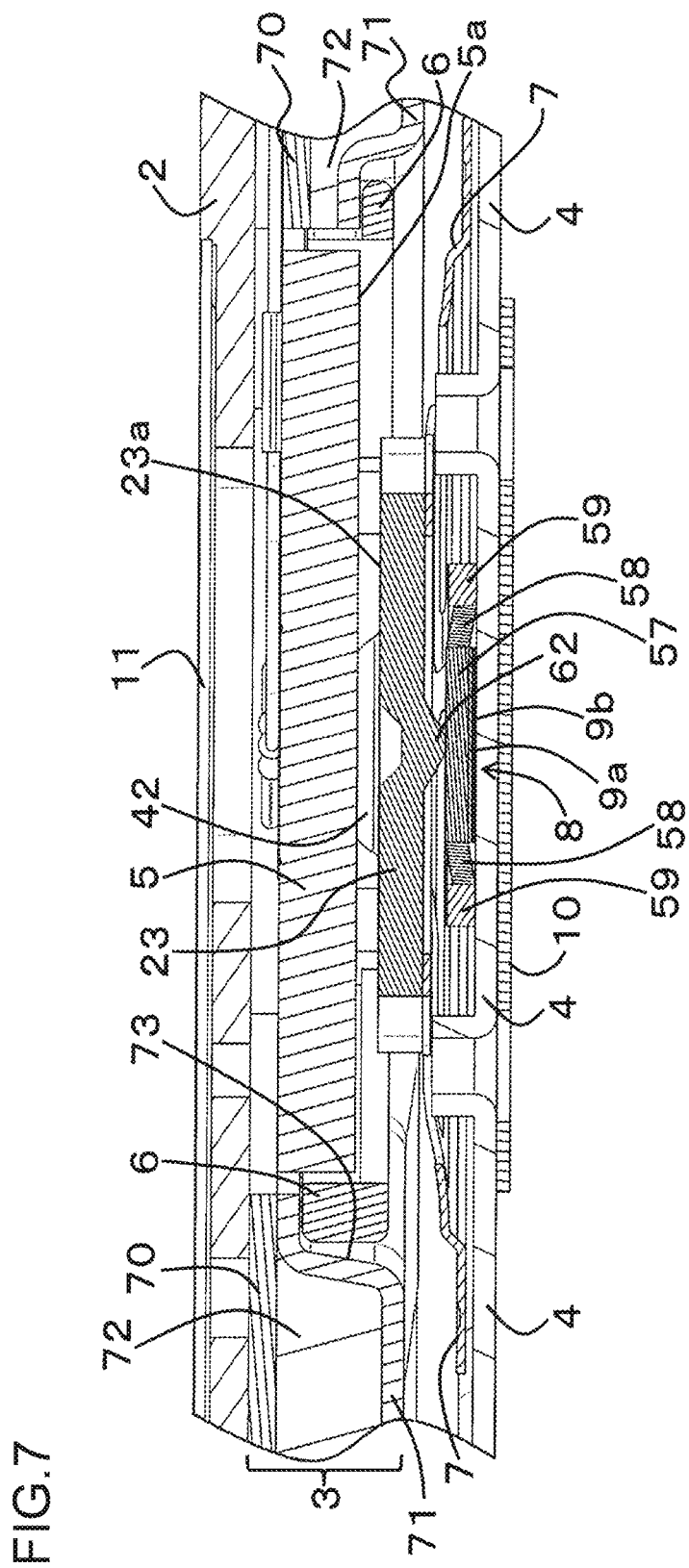
FIG. 7 Cross-sectional view of a part in a cross section along line A-A of FIG. 6 corresponding to a circle C1.

Further, among the members around the load cell 5 shown in FIG. 2, the leaf spring 7 and the receiving member 8 are attached to the bottom cover 4 side. Before describing a method of attaching the leaf spring 7 and the receiving member 8, the structure of the leaf spring 7 and the receiving member 8 will be described with reference to FIG. 6 and FIG. 7 in addition to FIG. 2 described above. FIG. 6 is a top plan view of the body composition meter 1 after assembly, while FIG. 7 is a cross-sectional view of a part in a cross section along line A-A of FIG. 6 corresponding to a circle C1 shown by a dot-dashed line. As shown in FIG. 2, the leaf spring 7 comprises a bottom cover attaching part 7a ("peripheral part" in the claims), an elastically deforming part 7b, and a bridge receiving part 7c. The bottom cover attaching part 7a is a peripheral part of the leaf spring 7, and is a part fixed to the bottom cover 4. The elastically deforming part 7b is a part with a tortuous shape which is provided on an inner peripheral side of the bottom cover attaching part 7a, and can elastically deform. The bridge receiving part 7c is a part provided on an inner peripheral side of the elastically deforming part 7b to receive the bridge 23. Further, as shown in FIG. 2 and FIG. 7, the receiving member 8 comprises: a plate-shaped part 57 made of an iron plate; a flexible elastic part 58 ("elastic part" in the claims) made of rubber provided on an outer periphery of the plate-shaped part 57; and an outer ring 59 ("outer frame part" in the claims) made of iron provided on an outer periphery of the flexible elastic part 58.

A method of attaching the receiving member 8 to the bottom cover 4 is as follows. More specifically, the low friction sheet 9a and the low friction sheet 9b are pasted on a lower surface of the receiving member 8 and an upper surface of the bottom cover 4, respectively, and then, the outer ring 59 of the receiving member 8 is welded to the bottom cover 4 so as to attach the receiving member 8 to the bottom cover 4. Thus, only the outer ring 59 is attached to the bottom cover 4 without attaching the plate-shaped part 57 and the flexible elastic part 58 of the receiving member 8 to the bottom cover 4.

Further, as shown in FIG. 2, the leaf spring 7 has a hole 53 in a central part thereof. The leaf spring 7 is attached to the bottom cover 4 by welding joint parts 52 at four locations thereof to the bottom cover 4 in a state where the receiving member 8 is contained in the hole 53.

The bridge 23, which together with the load cell 5 and the sensor holder 6 described above is attached to the reinforcement cover 3 side, is fixed with the small screws 54 to the leaf spring 7 attached to the bottom cover 4 side. Note that FIG. 2 shows only two small screws 54, but actually the number of small screws 54 is four. These small screws 54 are inserted from the lower surface side of the bottom cover 4 through holes 60 (so-called clearance holes) provided in the bottom cover 4. Further, the thread parts of the small screws 54 are inserted through holes 51 of the leaf spring 7 attached to the bottom cover 4, and are screwed into the threaded screw holes 41 of the bridge 23. Thus, the leaf spring 7 attached to the bottom cover 4 side is screwed to the bridge 23 attached to the reinforcement cover 3 side. According to this configuration, the elastically deforming part 7b of the leaf spring 7 is formed to be elastically deformable as described above, and therefore, this makes it possible to change the inclination of the bridge 23 relative to the bottom cover 4.

As described above, after the leaf spring 7 attached to the bottom cover 4 side is screwed to the bridge 23 attached to the reinforcement cover 3 side, the legs 10 shown in FIG. 1 are pasted on the lower surface of the bottom cover 4 so as to cover the holes 60 shown in FIG. 2. As described above, the leaf spring 7 is screwed to the bridge 23 attached to the reinforcement cover 3 side, and the reinforcement cover 3 is connected to the resin cover 2. Therefore, the leaf spring 7 is connected to the resin cover 2 side through the bridge 23, the load cell 5 and the reinforcement cover 3.

Next, referring to FIG. 7, the positional relationship between the members around the load cell 5 in the body composition meter 1 after assembly will be described. As shown in FIG. 7, when not loaded with the weight of a subject, the load cell 5 is supported by the bosses 42 provided on the upper surface 23a of the bridge 23, while (the lower surface 5a of) the load cell 5 and (the upper surface 23a of) the bridge 23 are in parallel to each other. Further, as shown in FIG. 7, in the body composition meter 1 after assembly, the pivot 62 of the bridge 23 is in contact with the plate-shaped member 57 of the receiving member 8.

Next, referring to FIG. 3 to FIG. 5 described above, the influence of the inclination between (the lower surface 5a of) the load cell 5 and (the upper surface 23a of) the bridge 23 on the output of the strain gauge 32 of the load cell 5 will be described. As shown in FIG. 5, when (the lower surface 5a of) the load cell 5 and (the upper surface 23a of) the bridge 23 are in parallel to each other, the weight of the subject is applied upward in a vertical direction from the leg 10 (refer to FIG. 1, FIG. 7, FIG. 10 and so on) to the lower surface 5a of the load cell 5 through the pivot 62 of the bridge 23 as shown by the solid line arrow and the dash line arrow of FIG. 5. However, when (the lower surface 5a of) the load cell 5 and (the upper surface 23a of) the bridge 23 are brought to a state where they are not in parallel (or are inclined) to each other, it leads to a state where the weight of the subject is not applied upward in a vertical direction to the load cell 5. Thus, when (the lower surface 5a of) the load cell 5 and (the upper surface 23a of) the bridge 23 are not in parallel to each other, the manner of strain of the strain generating part 35 of the load cell 5 changes compared with when they are in parallel to each other, thus causing an error in the output value of the stain gauge 32 of the load cell 5, consequently making it impossible for the body composition meter 1 to accurately measure the weight of the subject.

In contrast to the weight measurement device shown in the above Patent Document 1, the body composition meter 1 of the present embodiment is designed to make it possible to keep (the lower surface 5a of) the load cell 5 to be in parallel to (the upper surface 23a of) the bridge 23 without placing a thick rubber under the bridge, even when the resin cover 2 and the reinforcement cover 3 deflect due to the weight of the subject.

Figure 8:
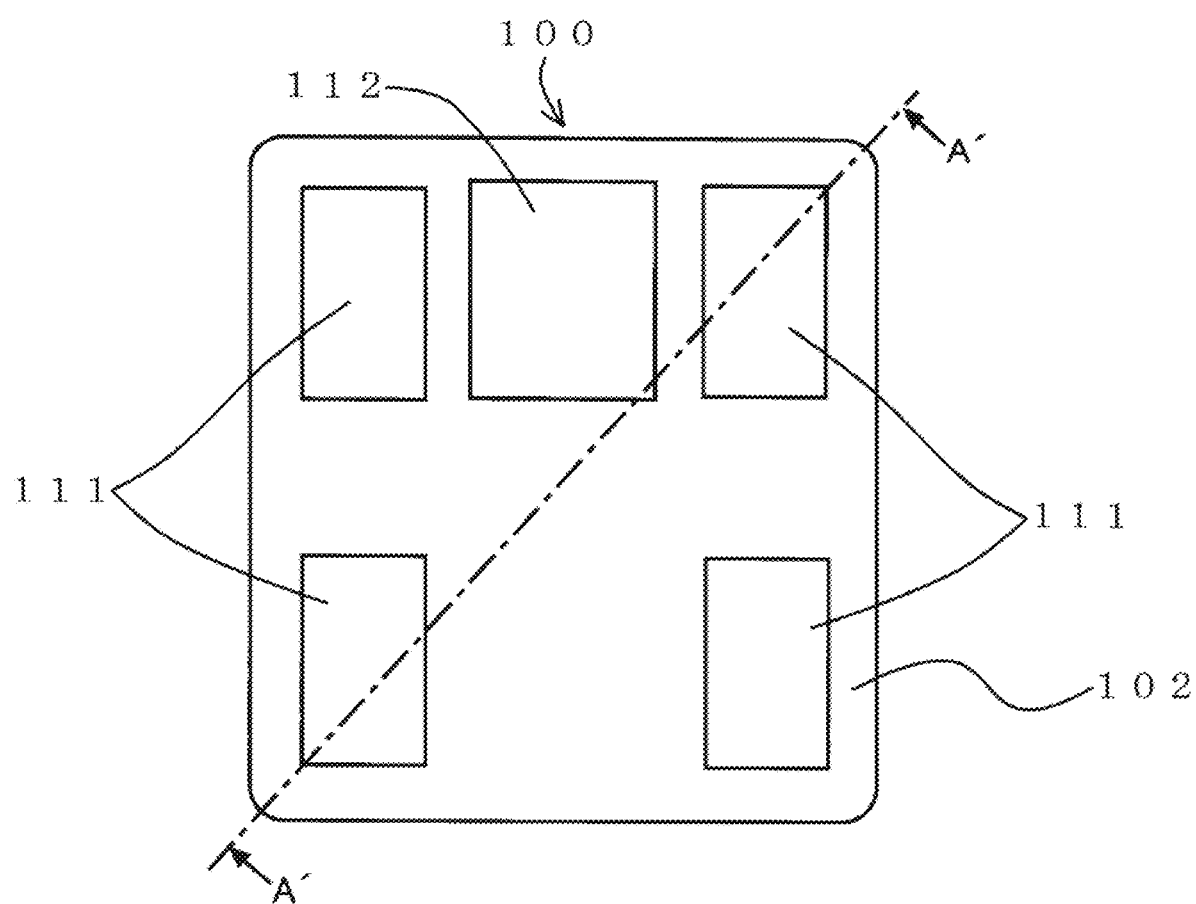
FIG. 8 Top plan view of a body composition meter according to a comparative example.
Figure 9:
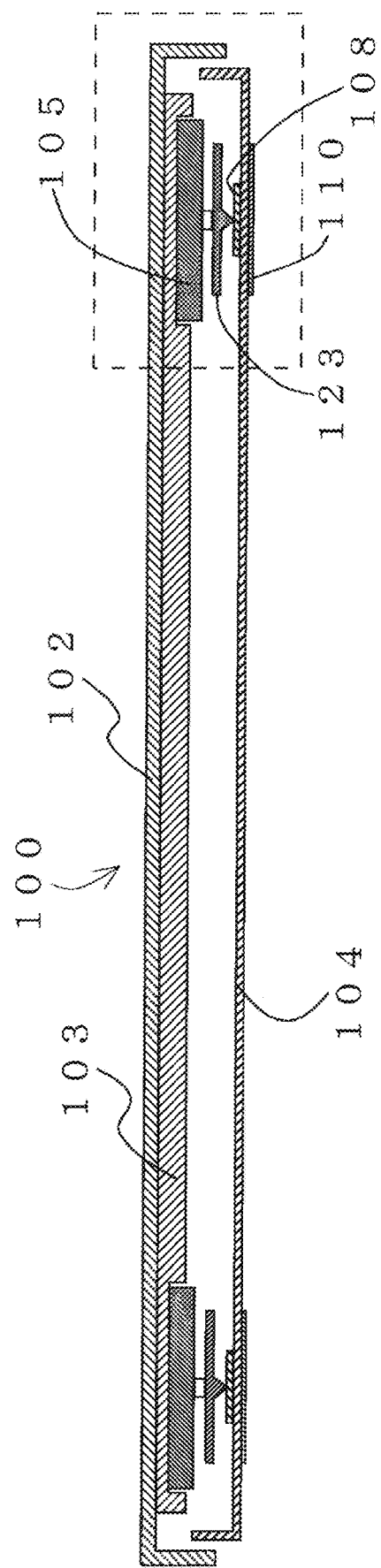
FIG. 9 Cross-sectional view of the body composition meter according to the comparative example along line A'-A' of FIG. 8 when not loaded with the weight of a subject.
Figure 10:
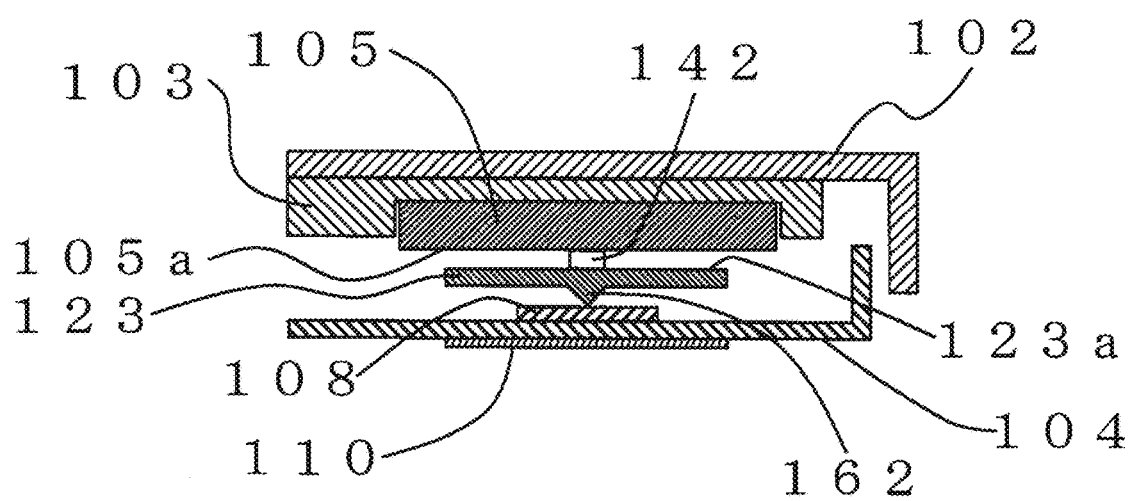
FIG. 10 Enlarged view of a part surrounded by a dashed line in FIG. 9.
Figure 11:
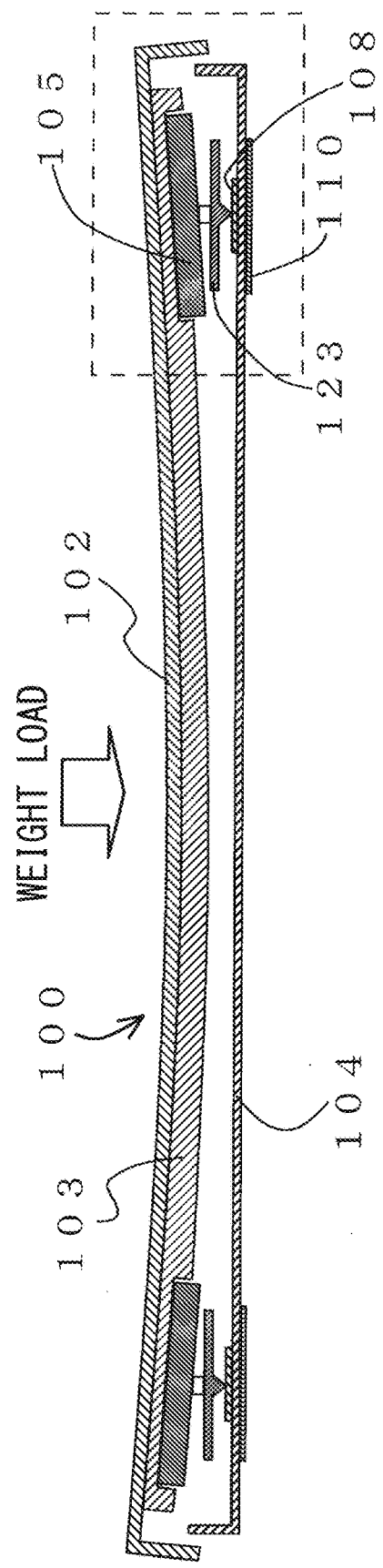
FIG. 11 Cross-sectional view of the body composition meter according to the comparative example along line A'-A' of FIG. 8 when loaded with the weight of the subject.
Figure 12:
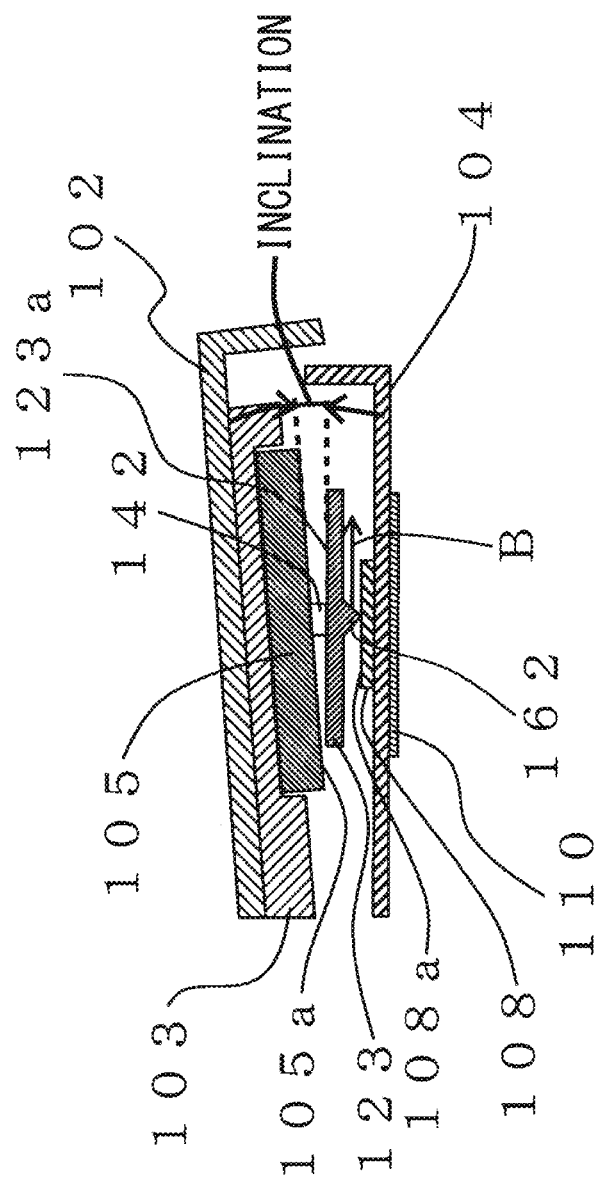
FIG. 12 Enlarged view of a part surrounded by a dashed line in FIG. 11.

The original idea to keep the load cell 5 to be in parallel to the bridge 23 will be described with reference to a body composition meter of a comparative example relative to the body composition meter 1 of the present embodiment. FIG. 8 is a top plan view of a body composition meter 100 of this comparative example, while FIG. 9 is a cross-sectional view of the body composition meter 100 along line A'-A' of FIG. 8 when not loaded with the weight of a subject. FIG. 10 is an enlarged view of a part surrounded by a dashed line in FIG. 9. FIG. 11 is a cross-sectional view of the body composition meter 100 along line A'-A' of FIG. 8 when loaded with the weight of the subject. FIG. 12 is an enlarged view of a part surrounded by a dashed line in FIG. 11.

In the body composition meter 100 of the comparative example in contrast to the body composition meter 1 of the present embodiment, low friction sheets 9a, 9b are not pasted on the lower surface of a receiving member 108 and the upper surface of a bottom cover 104. Further, in the body composition meter 100 of the comparative example in contrast to the body composition meter 1 of the present embodiment, the receiving member 108 is formed of a single member such as an iron plate or the like, and the entire receiving member 108 is fixed to the upper surface of the bottom cover 104. Thus, it is not possible to move the receiving member 108 in a horizontal direction relative to the bottom cover 104. Except for these parts, the body composition meter 100 of the comparative example is the same in configuration as the body composition meter 1 of the present embodiment. Note that in FIGS. 8, 111 and 112 designate electrodes and a display window of a display unit, respectively. Further, 110 in FIG. 9 to FIG. 12 designates a leg of the body composition meter 100, while 142 in FIG. 10 and FIG. 12 designates a boss of the body composition meter 100.

As shown in FIG. 11 and FIG. 12, according to the configuration of the body composition meter 100, the load cell 105 fixed to the reinforcement cover 103 inclines when the resin cover 102 and the reinforcement cover 103 deflect due to the weight of the subject. However, the pivot 162 of the bridge 123 fixed to the load cell 105 with rivets cannot be moved to outside the body composition meter 100 (in the direction shown by arrow B in FIG. 12) due to a friction force generated between it and the upper surface 108a of the receiving member 108, and therefore, as shown in FIG. 12, an inclination occurs between the lower surface 105a of the load call 105 and the upper surface 123a of the bridge 123. In this way, when the lower surface 105a of the load cell 105 and the upper surface 123a of the bridge 123 are brought to a state where they are not in parallel (or are inclined) to each other, it leads to a state where the weight of the subject is not applied upward in a vertical direction to the load cell 105. Therefore, the manner of strain of the load cell 105 in the strain region changes depending on the manner of deflection of the resin cover 102 and the reinforcement cover 103, thus making it impossible to obtain an accurate output of (the strain gauge of) the load cell 105. Therefore, it is not possible for the body composition meter 100 to accurately measure the weight of the subject.

Figure 13:
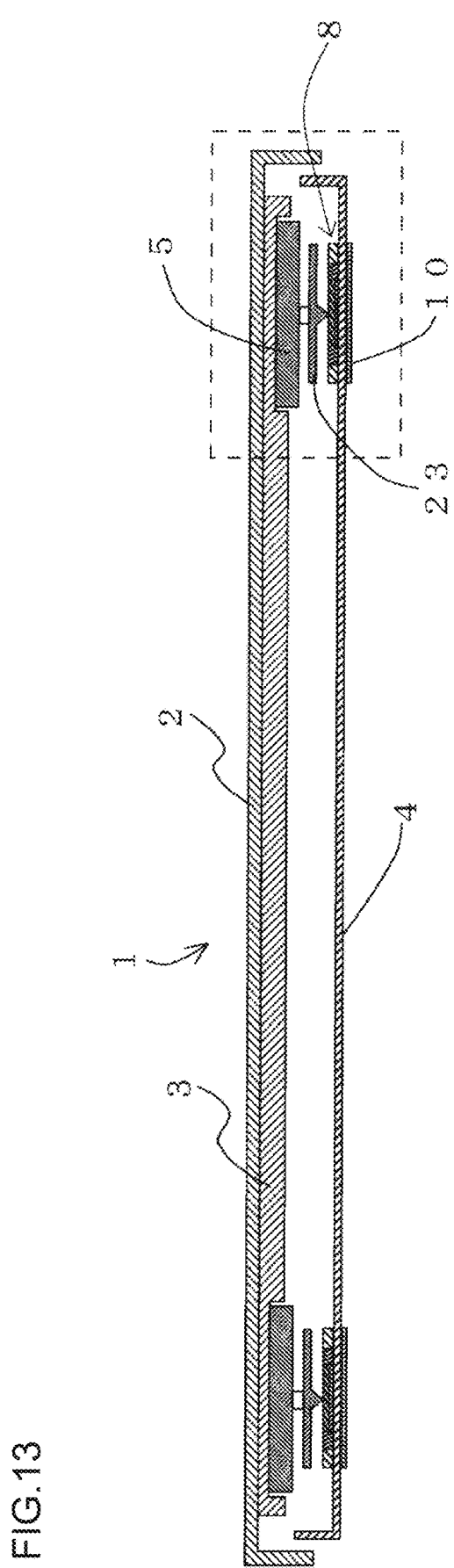
FIG. 13 Cross-sectional view of the present body composition meter along line A-A of FIG. 6 when not loaded with the weight of a subject.
Figure 14:
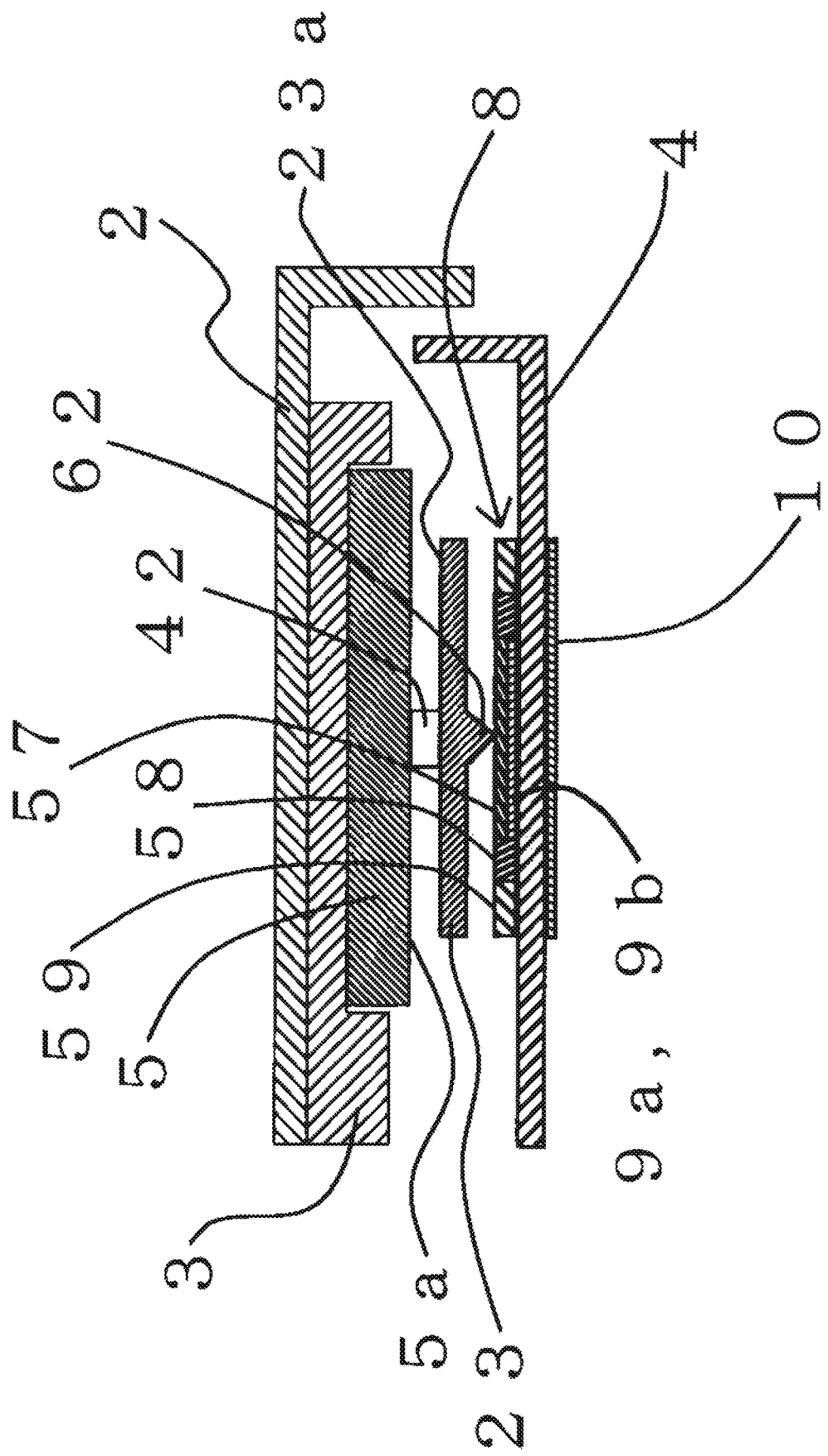
FIG. 14 Enlarged view of a part surrounded by a dashed line in FIG. 13.
Figure 15:
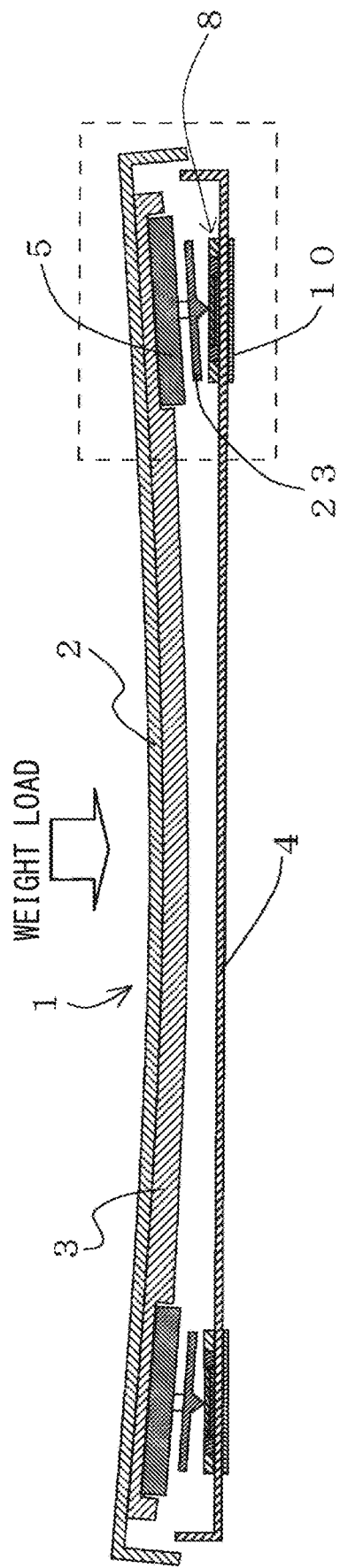
FIG. 15 Cross-sectional view of the present body composition meter along line A-A of FIG. 6 when loaded with the weight of the subject.
Figure 16:
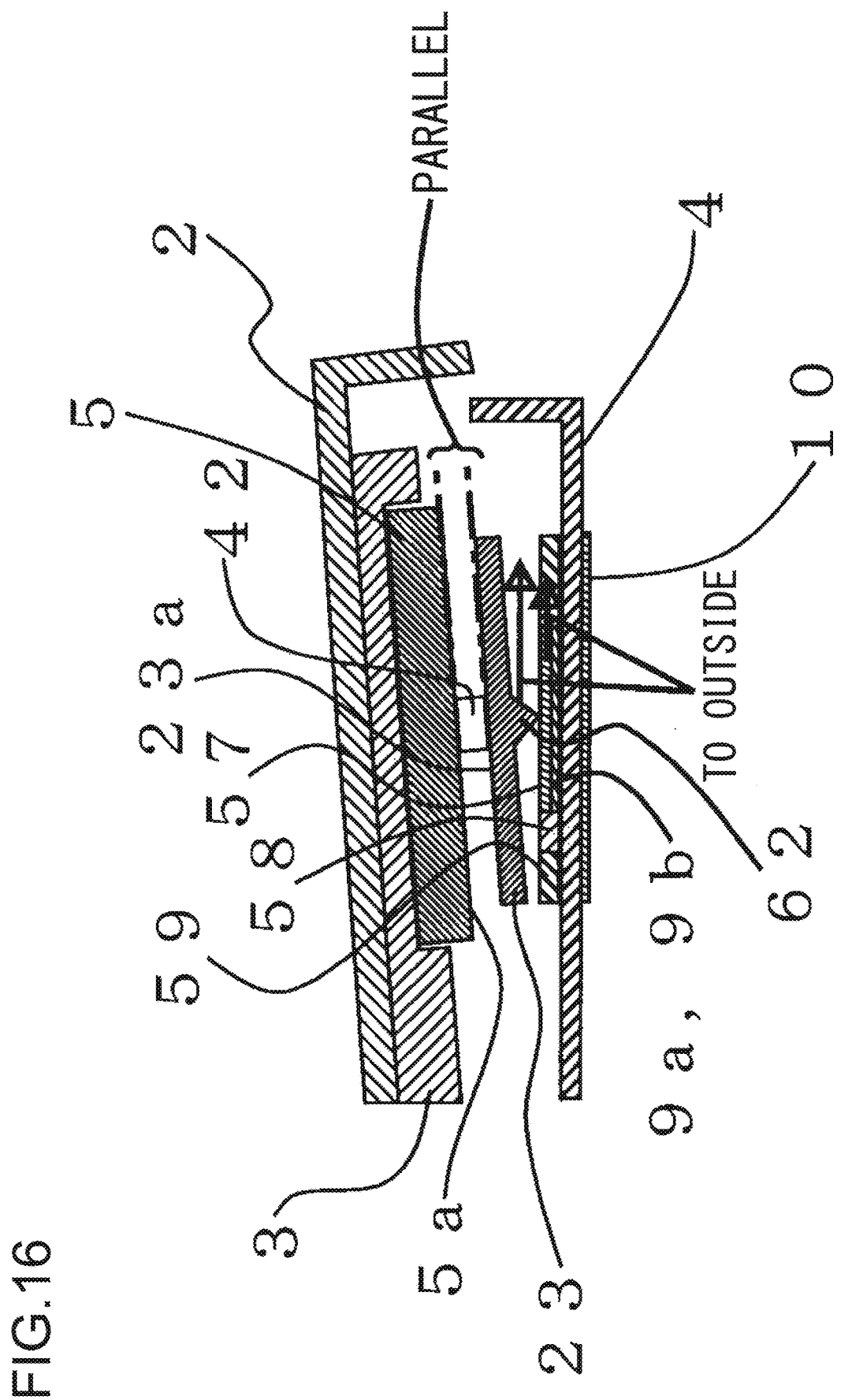
FIG. 16 Enlarged view of a part surrounded by a dashed line in FIG. 15.

On the other hand, according to the body composition meter 1 of the present embodiment, the lower surface 5a of the load cell 5 and the upper surface 23a of the bridge 23 can be kept in parallel to each other. The reason for this will be described with reference to FIG. 13 to FIG. 16. FIG. 13 is a cross-sectional view of the body composition meter 1 along line A-A of FIG. 6 when not loaded with the weight of a subject. FIG. 14 is an enlarged view of a part surrounded by a dashed line in FIG. 13. FIG. 15 is a cross-sectional view of the body composition meter 1 along line A-A of FIG. 6 when loaded with the weight of the subject. FIG. 16 is an enlarged view of a part surrounded by a dashed line in FIG. 15.

As shown in FIG. 14 and FIG. 16, the body composition meter 1 of the present embodiment has the low friction sheets 9a, 9b pasted on the lower surface of the receiving member 8 and the upper surface of the bottom cover 4 in contrast to the body composition meter 100 of the comparative embodiment. The friction coefficient of these low friction sheets 9a, 9b is set to satisfy the relationship that when the resin cover 2 and the reinforcement cover 3 deflect due to the weight of a subject, the friction force generated between (the low friction sheet 9a of) the lower surface of the plate-shaped part 57 of the receiving member 8 and (the low friction sheet 9b of) the upper surface of the bottom cover 4 is smaller than the friction force generated between the pivot 62 of the bridge 23 and the upper surface of the plate-shaped part 57 of the receiving member 8. Further, in the receiving member 8 of the body composition meter 1 of the present embodiment in contrast to the body composition meter 100 of the comparative example, only the part of the outer ring 59 is fixed to the bottom cover 4, and therefore, the plate-shaped part 57 of the receiving member 8 can be moved in a horizontal direction relative to (the upper surface and the lower surface of) the bottom cover 4.

As shown in FIG. 15 and FIG. 16, in the body composition meter 1 of the present embodiment, when the resin cover 2 and the reinforcement cover 3 deflect due to the weight of the subject, the load cell 5 fixed to the reinforcement cover 3 inclines, and as it inclines, the pivot 62 of the bridge 23 fixed to the load cell 5 attempts to move to outside the body composition meter 1 (in the direction shown by arrow in FIG. 16). Here, the low friction sheets 9a, 9b function so that when the resin cover 2 and the reinforcement cover 3 deflect due to the weight of the subject, the friction force acting between the lower surface of the receiving member 8 and the upper surface of the bottom cover 4 (more precisely, friction force acting between the low friction sheet 9a pasted on the lower surface of the plate-shaped part 57 of the receiving member 8 and the low friction sheet 9b pasted on the upper surface of the bottom cover 4) is smaller than the friction force generated between the pivot 62 of the bridge 23 and the upper surface of (the plate-shaped part 57 of) the receiving member 8. Thus, when the resin cover 2 and the reinforcement cover 3 deflect, and the load cell 5 inclines due to the weight of the subject, the plate-shaped part 57 of the receiving member 8 moves to outside the body composition meter 1 (in a horizontal direction relative to (the upper surface and the lower surface) of the bottom cover 4) as shown in FIG. 16, the pivot 62 moves to outside the body composition meter 1, therefore causing a change in the inclination of the bridge 23 relative to the bottom cover 4, although due to the influence of the friction force generated between the pivot 62 and the upper surface of the plate-shaped part 57, the position of the pivot 62 of the bridge 23 relative to the plate-shaped part 57 (of the receiving member 8) is unchanged from before loaded with the weight of the subject.

In this way, when the resin cover 2 and the reinforcement cover 3 deflect due to the weight of the subject, the upper surface 23a of the bridge 23 can be kept in parallel to the lower surface 5a of the load cell 5, and therefore, the weight of the subject can be applied upward in a vertical direction to the load cell 5 through the bridge 23. Thus, according to the body composition meter 1, when the resin cover 2 and the reinforcement cover 3 deflect due to the weight of the subject, it is possible to obtain an output from the load cell 5 due to a deflection of deformed shape of the strain generating part 35 without twisting (deformed shape of the strain generating part 35 similar to when the deflection of the resin cover 2 and the reinforcement cover 3 does not occur), therefore making it possible to obtain an accurate output of the load cell 5. Thus, the weight of the subject can be accurately measured. In contrast to this, as shown in FIG. 11 and FIG. 12, when the upper surface 123a of the bridge 123 cannot be kept in parallel to the lower surface 105a of the load cell 105, and the weight of the subject cannot be applied upward in a vertical direction to the load cell 105 through the bridge 123, the strain generating part of the load cell 105 causes a deflection of deformed shape with twisting, thus consequently causing the output from the load cell 105 to be an output including components due to the twisting of the strain generating part, making it impossible to obtain an accurate output of the load cell 105.

Note that the manner of deflection of the resin cover 2 and the reinforcement cover 3 changes not only with the magnitude of the weight of the subject, but also with the size of the feet of the subject, and with the position in the upper surface of the resin cover 2 at which both feet of the subject are placed. However, according to the body composition meter 1 of the present embodiment, regardless of the manner of deflection of the resin cover 2 and the reinforcement cover 3, it is possible to obtain an output from (the strain gauge 32 of) the load cell 5 due to the deflection of deformed shape without twisting of the strain generating part 35, and therefore, an accurate output of the load cell 5 can be obtained.

Further, in the receiving member 8 of the body composition meter 1 of the present embodiment, as described above, only the part of the outer ring 59 is fixed to the bottom cover 4, while as shown in FIG. 16, the flexible elastic part 58 made of rubber is provided between the outer ring 59 and the plate-shaped part 57. When the weight of the subject is applied to the resin cover 2 and the reinforcement cover 3 to cause a horizontal force to be generated in the plate-shaped part 57 through the pivot 62 of the bridge 23, the flexible elastic part 58 made of rubber deflects, while when the weight of the subject is stopped from being applied to the resin cover 2 and the reinforcement cover 3, the flexible elastic part 58 serves to bring the plate-shaped part 57 back to its position before the weight of the subject is applied. More specifically, when the subject steps down from the top of the resin cover 2 to cause the weight of the subject to be stopped from being applied to the resin cover 2 and the reinforcement cover 3, the deflection of the resin cover 2 and the reinforcement cover 3 disappears as shown in FIG. 13 and FIG. 14. Thus, in contrast to when loaded with the weight of the subject, the inclination of the load cell 5 fixed to the reinforcement cover 3 disappears (the load cell 5 returns from the state shown in FIG. 16 back to the state shown in FIG. 14). At this time, along with the movement of the load cell 5 from the state shown in FIG. 16 back to the state shown in FIG. 14, the elastic force of the flexible elastic part 58 of the receiving member 8 brings the plate-shaped part 57 to its position before loaded with the weight of the subject (in the direction opposite to the arrow in FIG. 16). Thus, the pivot 62 of the bridge 23 moves to inside the body composition meter 1 (in the direction opposite to the arrow in FIG. 16), and the inclination of the bridge 23 relative to the bottom cover 4 returns to the inclination before loaded with the weight of the subject as shown in FIG. 14.

Note that even without pasting the low friction sheets 9a, 9b on the lower surface of the receiving member 8 and the upper surface of the bottom cover 4 as in the body composition meter 1 of the present embodiment, it is possible to keep the upper surface of the bridge to be in parallel to the lower surface of the load cell when the weight of the subject is applied, similarly as in the body composition meter 1 of the present embodiment, if a method such as coating a lubricating agent on (particularly the top part of) the pivot of the bridge is used to allow the pivot in contact with the receiving member or the upper surface of the bottom cover to slide. However, such a configuration causes the pivot loaded with a point load (concentrated load) to move in a horizontal direction relative to (the upper surface of) the bottom cover, and therefore, the pivot is likely to wear, causing the device (particularly the pivot) to have a low durability. In contrast, according to the body composition meter 1 of the present embodiment, the plate-shaped part 57 of the receiving member 8 loaded with the load from the leg 10 in the form of surface load moves in a horizontal direction relative to (the upper surface of) the bottom cover 4, and therefore, the wear between the parts and members is less likely to occur compared with the case of sliding the pivot as described above.

Next, the original idea used in the body composition meter 1 to achieve the reduction in thickness and the reduction in weight of the entire device, while securing its accuracy, will be described. First, in the body composition meter 1 as described above, the bridge 23 is provided with the pivot 62 which is a fulcrum to make it possible to change the inclination of the bridge 23 and which is in contact with the upper surface of the plate-shaped part 57 of the receiving member 8, while the flexible elastic part 58 is provided between the outer ring 59 and the plate-shaped part 57 of the receiving member 8, and further the low friction sheets 9a, 9b to enable the receiving member 8 to move in a horizontal direction relative to the bottom cover 4 are pasted on the lower surface of the plate-shaped part 57 of the receiving member 8 and the upper surface of the bottom cover 4. The functions of these parts and members, in contrast to the weight measurement device shown in Patent Document 1, make it possible without placing a thick rubber under the bridge to keep the upper surface 23a of the bridge 23 to be in parallel to the lower surface 5a of the load cell 5 when the resin cover 2 and the reinforcement cover 3 deflect due to the weight of a subject. Thus, it is possible to achieve the reduction in thickness and the reduction in weight of the entire device as compared with the conventional weight measurement device shown in Patent Document 1.

Further, this body composition meter 1 uses, as the housing, the reinforcement cover 3 formed by combining a metal and a resin. This point will be described with reference to FIG. 7 described above. Normally, housings of a body composition meter or a weight scale use an iron plate (pressed part) or a resin (injection molded component). In order to allow a product using these housings to have a sufficient strength, the entire product is required to have a thickness of 30 mm or more. Thus, this body composition meter 1 uses the reinforcement cover 3 formed by combining the metal and the resin in order to achieve the reduction in thickness and the reduction in weight of the housing and the entire device while maintaining its required strength. As shown in FIG. 7, the reinforcement cover 3 comprises an iron plate cover 70 ("upper surface cover made of metal" in the claims), an iron plate base 71 ("bottom surface cover made of metal" in the claims) and a resin layer 72 provided between them. Many fine recessed parts are formed by surface treatment in the lower surface of the iron plate cover 70 and the upper surface of the iron plate base 71. These recessed parts have a diameter of, for example, 10 to 400 nm. When the iron plate cover 70, the resin layer 72 and the iron plate base 71 are combined, the resin gets into the many fine recessed parts provided in the lower surface of the iron plate cover 70 and the upper surface of the iron plate base 71 so as to bond the iron plate cover 70, the resin layer 72 and the iron plate base 71.

As described above, the reinforcement cover 3 is formed by the iron plate cover 70, the iron plate base 71 and the resin layer 72 provided between them, and the resin is filled into the many fine recessed parts provided in the lower surface of the iron plate cover 70 and the upper surface of the iron plate base 71 so as to bond the iron plate cover 70, the resin layer 72 and the iron plate base 71, thereby making it possible for the reinforcement cover 3 to be a strong housing (hard to deflect) even if it is thin. The reinforcement cover 3 has a thickness of, for example, 5 to 7 mm. Further, the reinforcement cover 3 has the resin layer 72 between the iron plate cover 70 and the iron plate base 71, and therefore, this can achieve the reduction in weight of the housing as compared with the conventional housing which is formed by only a metallic plate such as an iron plate. The use of the thin and low weight reinforcement cover 3 as the housing of the body composition meter 1, as described above, can achieve the reduction in thickness and the reduction in weight of the entire device of the body composition meter 1.

Next, referring to FIG. 2, the reason why the leaf spring 7 is used to attach the load cell 5 to the bottom cover 4 will be described. Note that, more precisely, by welding the joint parts 52 of the leaf spring 7 shown in FIG. 2 to the bottom cover 4, the bottom cover attaching part 7a of the leaf spring 7 is attached to the bottom cover 4, and also the bridge receiving part 7c of the leaf spring 7 is connected to the bridge 23. Further, the bridge 23 is connected to the strain generating body 31 of the load cell 5. In other words, the load cell 5 is attached to the bottom cover 4 through the bridge 23 and the lead spring 7. As described above, the connection between the leaf spring 7 and the bridge 23 is done with the four small screws 54, while the connection between the bridge 23 and the strain generating body 31 of the load cell 5 is done with the rivets 43.

The first reason why the leaf spring 7 is used to fix the load cell 5 to the bottom cover 4 as described above is to make it hard for the bottom cover 4 to be disconnected when a user lifts the resin cover 2 side. The connection of the leaf spring 7 and the bridge 23 using the small screws 54 as described above can make it hard for the bridge 23 and the leaf spring 7 fixed to the bottom cover 4 to be disconnected from each other when a user lifts the resin cover 2 side, which therefore can make it hard for the bottom cover 4 to be disconnected.

Further, the second reason why the leaf spring 7 is used to fix the load cell 5 to the bottom cover 4 is that when the body composition meter 1 is loaded with the weight of a subject, the load cell 5 deflects (strains), while if the load cell 5 and the bottom cover 4 are firmly attached to each other, it hinders the deflection of the load cell 5 (strain of the strain generating part 35) and badly affects the performance of the body composition meter 1. Therefore, in the body composition meter 1, the leaf spring 7 is designed to have a part which supports the lower surface of the bridge 23 and which is formed to be elastically deformable, while the load cell 5 and the bridge 23 are movably attached to the bottom cover 4 through the leaf spring 7, so as to use the elasticity of the leaf spring 7 to prevent the hindrance of the deflection of the load cell 5 (the strain of the strain generating part 35).

Figure 17:
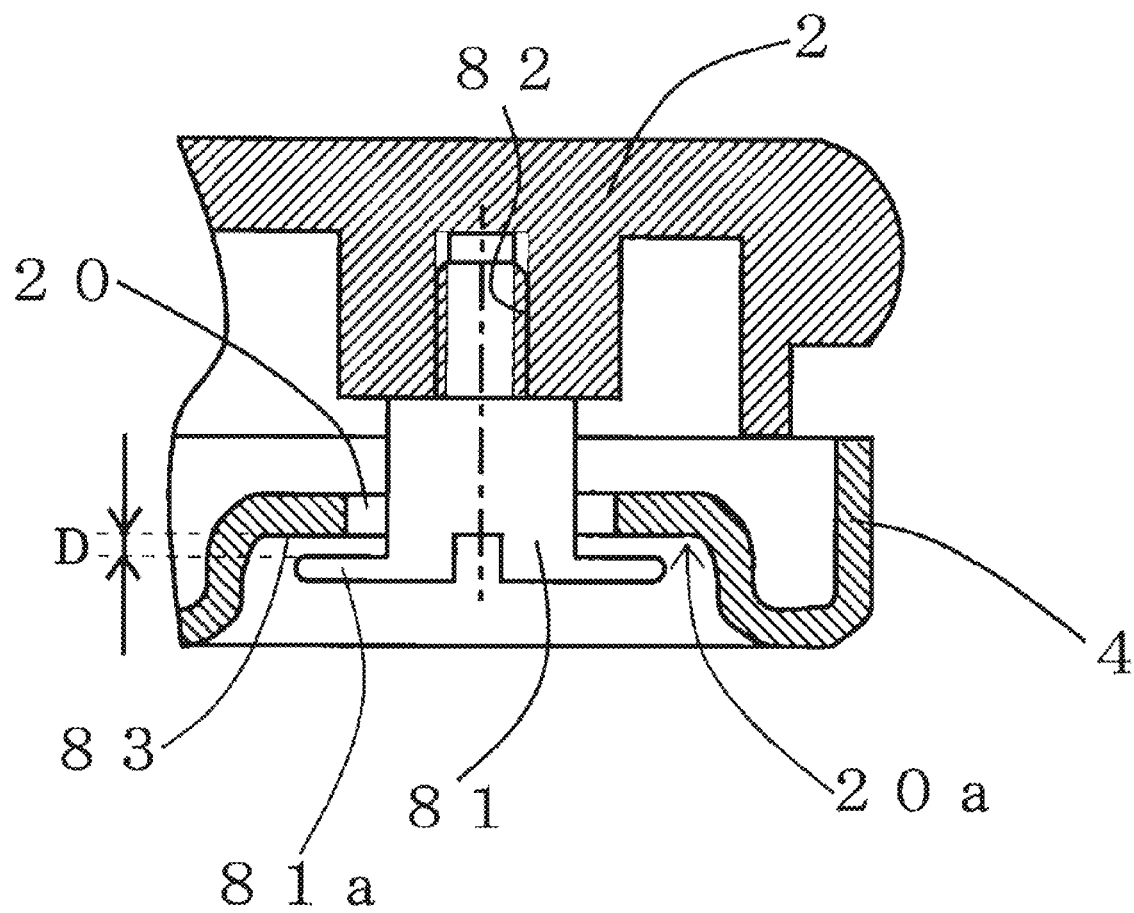
FIG. 17 Cross-sectional view of a part in a cross section along line A-A of FIG. 6 corresponding to a circle C2.

As described above, the use of the leaf spring 7 to attach the load cell 5 to the bottom cover 4 can make it hard for the bottom cover 4 to be disconnected when a user lifts the resin cover 2 side. However, when the resin cover 2 side is strongly pulled, the leaf spring 7 is stretched to its limit and consequently does not return to its original state. Thus, the body composition meter 1 comprises a separation prevention screw 81 shown in FIG. 17 as a separation prevention member to prevent the bottom cover 4 from being separated from the resin cover 2 and the reinforcement cover 3 by a given distance or more. FIG. 17 is a cross-sectional view of a part in a cross section along line A-A of FIG. 6 corresponding to a circle C2 shown by a dashed line.

The separation prevention screw 81 described above is inserted from a hole 20 of the bottom cover 4 shown in FIG. 2 and FIG. 17, and is screwed into a screw hole 82 (refer to FIG. 17) provided in the resin cover 2. Further, as shown in FIG. 17, a recessed part 20a is provided around the hole 20 of the bottom cover 4, and a gap is present between a screw head 81a of the separation prevention screw 81 and a surface 83 of the recessed part 20a in the state after the separation prevention screw 81 is attached to the resin cover 2. When the resin cover 2 side is pulled in this state, the screw head 81a of the separation prevention screw 81 attached to the resin cover 2 side is hooked to (the surface 83 of) the recessed part 20a of the bottom cover 4, thereby preventing the bottom cover 4 from being separated from the resin cover 2 and the reinforcement cover 3 by a given distance (distance D (refer to FIG. 17) of the gap between the screw head 81a and the surface 83 of the recessed part 20a) or more. The distance D is set to a distance which prevents the leaf spring 7 fixed to the bottom cover 4 side from being stretched to its limit. Thus, even if the resin cover 2 side is strongly pulled, the distance of the resin cover 2 and the reinforcement cover 3 from the bottom cover 4 can be kept short, therefore making it possible to prevent the leaf spring 7 connected to both the resin cover 2 side and the bottom cover 4 side from being stretched to its limit.

As described above, according to the body composition meter 1 of the present embodiment, even if the pivot 62 becomes unable to move in a horizontal direction relative to the plate-shaped part 57 of the receiving member 8 due to the friction force generated between the pivot 62 of the bridge 23 and the upper surface of the plate-shaped part 57 of the receiving member 8 when the resin cover 2 and the reinforcement cover 3 deflect due to the weight of a subject, it is possible to move the plate-shaped part 57 of the receiving member 8 in a horizontal direction relative to the bottom cover 4 due to the function of the sliding part (the low friction sheet 9a pasted on the lower surface of the plate-shaped part 57 of the receiving member 8 and the low friction sheet 9b pasted on the upper surface of the bottom cover 4) provided between the lower surface of the plate-shaped part 57 of the receiving member 8 and the upper surface of the bottom cover 4. Therefore, the inclination of the bridge 23 relative to the bottom cover 4 can be changed by moving the pivot 62 in a horizontal direction relative to the bottom cover 4. Thus, when the resin cover 2 and the reinforcement cover 3 deflect due to the weight of the subject, the upper surface 23a of the bridge 23 can be kept in parallel to the lower surface 5a of the load cell 5, similarly as when the resin cover 2 and the reinforcement cover 3 do not deflect, making it possible to stably apply an upward force from the bridge 23 in a vertical direction to the load cell 5. Therefore, regardless of the manner of deflection of the resin cover 2 and the reinforcement cover 3, an accurate output from the strain gauge 32 of the load cell 5 can be obtained, making it possible to accurately measure the weight of the subject. In addition, in contrast to the weight measurement device 200 shown in Patent Document 1, a thick rubber is not required to be placed under the bridge, therefore making it possible to achieve the reduction in thickness of the entire device.

Further, according to the body composition meter of the present embodiment, the friction coefficient of the sliding part (the low friction sheet 9a pasted on the lower surface of the plate-shaped part 57 of the receiving member 8 and the low friction sheet 9b pasted on the upper surface of the bottom cover 4) provided between the lower surface of the plate-shaped part 57 of the receiving member 8 and upper surface of the bottom cover 4 is set to satisfy the relationship that when the resin cover 2 and the reinforcement cover 3 deflect due to the weight of a subject, the friction force acting between the lower surface of the receiving member 8 and the upper surface of the bottom cover 4 is smaller than the friction force generated between the pivot 62 of the bridge 23 and the upper surface of the plate-shaped part 57 of the receiving member 8. Thus, when the resin cover 2 and the reinforcement cover 3 deflect due to the weight of the subject, the plate-shaped part 57 of the receiving member 8 can be reliably moved in a horizontal direction relative to the bottom cover 4, while maintaining the contact position of the pivot 62 on the upper surface of the plate-shaped part 57 of the receiving member 8. Therefore, the inclination of the bridge 23 relative to the bottom cover 4 can be reliably changed by moving the pivot 62 in a horizontal direction relative to the bottom cover 4.

Further, according to the body composition meter 1 of the present embodiment, the sliding part described above uses the low friction sheets 9a, 9b made of fluorocarbon resin pasted on the lower surface of the plate-shaped part 57 of the receiving member 8 and the upper surface of the bottom cover 4. Thus, it is easy to reduce the friction force acting between the lower surface of the receiving member 8 and the upper surface of the bottom cover 4 when the resin cover 2 and the reinforcement cover 3 deflect due to the weight of a subject, and furthermore, it is possible to achieve the reduction in thickness and the reduction in weight of the entire device as compared with the weight measurement device 200 of Patent Document 1 which places a thick rubber under the bridge.

Further, according to the body composition meter 1 of the present embodiment, the receiving member 8 comprises: the plate-shaped part 57 in contact with the pivot 62 of the bridge 23; the flexible elastic part 58 made of rubber provided on an outer peripheral side of the plate-shaped part 57; and the outer ring 59 provided on an outer peripheral side of the flexible elastic part 58, in which only the outer ring 59 is attached to the bottom cover 4 without attaching the plate-shaped part 57 and the flexible elastic part 58 to the bottom cover 4. This configuration makes it possible that the plate-shaped part 57 of the receiving member 8 can move in a horizontal direction relative to the bottom cover 4, and furthermore that when the state in which the resin cover 2 and the reinforcement cover 3 are loaded with the weight of a subject is changed to the state in which they are not loaded with the weight of the subject, the elastic force of the flexible elastic part 58 can bring the plate-shaped part 57 back to its position before loaded with the weight of the subject.

Furthermore, the body composition meter 1 of the present embodiment further comprises the leaf spring 7 to attach the bridge 23 to the bottom cover 4 side, in which the leaf spring 7 has a peripheral portion (bottom cover attaching part 7a) fixed to the bottom cover 4, and is formed to be elastically deformable. Since the leaf spring 7 is thus formed to be elastically deformable, it becomes possible to change the inclination of the bridge 23 relative to the bottom cover 4. Further, by forming the leaf spring 7 to be elastically deformable and by fixing the load cell 5 and the bridge 23 to the bottom cover 4 through the leaf spring 7 as described above, the elasticity of the leaf spring 7 can be used to prevent the hindrance of the deflection of the load cell 5 (the strain of the strain generating part 35).

Further, the body composition meter 1 of the present embodiment has the leaf spring 7 connected to the resin cover 2 side, and further comprises the separation prevention screw 81 to prevent the bottom cover 4 from being separated from the resin cover 2 by a given distance or more, in which the given distance is set to a distance to prevent the leaf spring 7 fixed to the bottom cover 4 side from being stretched to its limit. Thus, even if the resin cover 2 side is strongly pulled, the distance of the resin cover 2 from the bottom cover 4 can be kept short, therefore making it possible to prevent the leaf spring 7 connected to both the resin cover 2 side and the bottom cover 4 from being stretched to its limit.

Further, according to the body composition meter 1 of the present embodiment, the reinforcement cover 3 comprises the iron plate cover 70, the iron plate base 71 and the resin layer 72 provided between them, and many fine recessed parts are provided in the lower surface of the iron plate cover 70 and the upper surface of the iron plate base 71, while resin of the resin layer 72 is filled into these many fine recessed parts so as to bond the iron plate cover 70, the resin layer 72 and the iron plate base 71. Thus, by filling the resin into the many fine recessed parts provided in the lower surface of the iron plate cover 70 and the upper surface of the iron plate base 71 so as to bond the iron plate cover 70, the resin layer 72 and the iron plate base 71, the reinforcement cover 3 can be a strong housing even if it is thin. Further, the reinforcement cover 3 has the resin layer 72 between the iron plate cover 70 and the iron plate base 71, and therefore, it is possible to achieve the reduction in weight of the housing as compared with the conventional housing which is formed by only a metallic plate such as an iron plate. As described above, the use of the thin and low weight reinforcement cover 3 as the housing of the body composition meter 1 can achieve the reduction in thickness and the reduction in weight of the entire device of the body composition meter 1.

MODIFIED EXAMPLES

It is to be noted that the present invention is not limited to each exemplary embodiment described above, and various modifications are possible within the spirit and scope of the present invention. Next, modified examples of the present invention will be described.

Modified Example 1

The above embodiment has described an example, in which the weight measurement device of the present invention is a body composition meter 1 with a function to measure the body composition of a subject. However, the weight measurement device of the present invention is not limited to this, and can be, for example, a weight scale without a function to measure the body composition of the subject, and can also be a weight measurement device such as an electronic scale for cooking or the like which measures a weight other than that of a human body.

Modified Example 2

The above embodiment has shown an example, in which the "sliding part" in the claims is the low friction sheets 9a, 9b. However, the "sliding part" in the weight measurement device of the present invention is not limited to this, and can be any which has a friction force to enable the plate-shaped part of the receiving member to move relative to the bottom cover when a horizontal force is generated in the plate-shaped part. For example, it can be one which is formed by subjecting at least one of the lower surface of the receiving member (for example, a part corresponding to the plate-shaped part 57 of the receiving member 8 of the present embodiment) and the upper surface of the bottom cover to plating treatment to reduce the friction coefficient. Further, the "sliding part" described above can be, for example, resin such as fluorocarbon resin coated on at least one of the lower surface of the receiving member (for example, a part corresponding to the plate-shaped part 57 of the receiving member 8 of the present embodiment) and the upper surface of the bottom cover.

Further, the above embodiment has shown an example, in which the low friction sheets 9a, 9b are sheets made of fluorocarbon resin. However, the low friction sheet used as the "sliding part" is not limited to this, and can be, for example, a sheet made of resin other than fluorocarbon resin. Furthermore, the above embodiment has shown an example, in which the low friction sheets 9a, 9b are pasted on both the lower surface of (the plate-shaped part 57 of) the receiving member 8 and the upper surface of the bottom cover 4. However, it is not limited to this, and it is also possible to paste a low friction sheet on only either of the lower surface of (the plate-shaped part of) the receiving member and the upper surface of the bottom cover.

Modified Example 3

Figure 18:
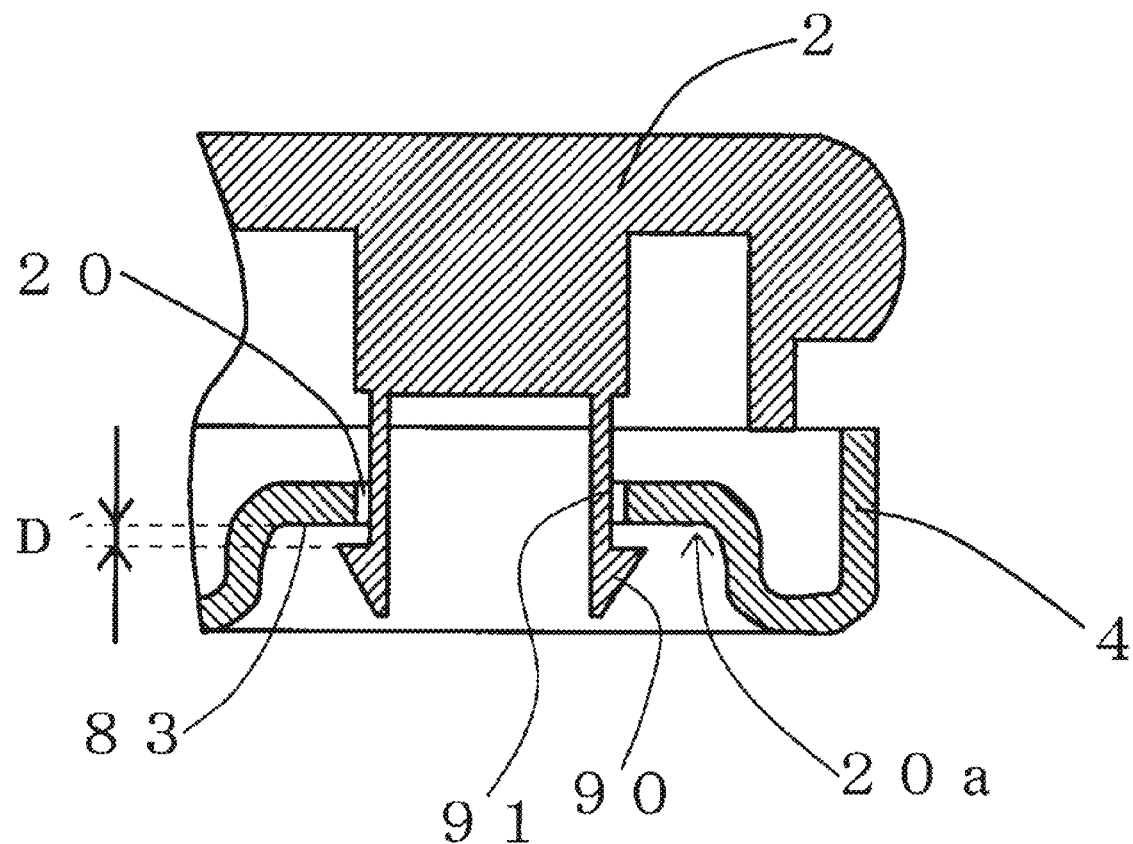
FIG. 18 Cross-sectional view of a part around a leg part in a body composition meter according to a Modified Example 3 of the present invention.

The above embodiment has shown an example, in which the "separation prevention member" in the claims is the separation prevention screw 81. However, the "separation prevention member" is not limited to this, and can be a member with a function to prevent the bottom cover 4 from being separated from the resin cover 2 and the reinforcement cover 3 by a given distance or more. For example, as shown in FIG. 18, the "separation prevention member" can be a removal prevention part 91 having a locking hook 90 and integrally formed with the resin cover 2. The removal prevention part 91 with the locking hook 90 is pressed into the hole 20 of the bottom cover 4 when the body composition meter 1 is assembled. According to this configuration, when the resin cover 2 side is pulled, the locking hook 90 of the removal prevention part 91 provided on the resin cover 2 is hooked by (the surface 83) of the recessed part 20a of the bottom cover 4 so as to prevent the bottom cover 4 from being separated from the resin cover 2 and the reinforcement cover 3 by a given distance (distance D' (refer to FIG. 18) between the locking hook 90 and the surface 83 of the recessed part 20a) or more.

Further, the above embodiment has shown an example, in which the separation prevention screw 81 is screwed into the screw hole 82 provided in the resin cover 2 and attached to the resin cover. However, the separation prevention screw can be screwed into a screw hole provided in the reinforcement cover and attached to the reinforcement cover.

Modified Example 4

The above embodiment has shown an example, in which the "upper surface cover made of metal" and the "bottom surface cover made of metal" in the claims are the iron plate cover 70 and the iron plate base 71. However, the "upper surface cover made of metal" and the "bottom surface cover made of metal" are not limited to this, and can be, for example, plates made of metal such as aluminum, copper, stainless steel or the like.

Modified Example 5

In the above embodiment, the bottom cover 4 is designed to have almost the same area as the entire device, and the four legs 10 are provided at positions corresponding to the load cells 5 in the bottom cover 4. However, it is not limited to this configuration. For example, it is possible to provide four combinations each of which has the bottom cover, the leg and the peripheral components of the load cell (load cell, bridge, sensor holder, leaf spring, receiving member and low friction sheets), each combination forming a unit, and to attach the combinations to the reinforcement cover. The upper and lower surfaces of these units have an area of, for example, about φ50 mm.

DESCRIPTION OF THE REFERENCE NUMERALS

1 Body composition meter
2 Resin cover (upper surface cover)
3 Reinforcement cover
4 Bottom cover (bottom surface cover)
5 Load cell
7 Leaf spring
8 Receiving member
9a, 9b Low friction sheets (sliding part, sheets made of resin, sheets made of fluorocarbon resin)
23 Bridge
31 Strain generating body
32 Strain gauge
57 Plate-shaped part
58 Flexible elastic part (elastic part)
59 Outer ring (outer frame part)
62 Pivot
70 Iron plate cover (upper surface cover made of metal)
71 Iron plate base (bottom surface cover made of metal)
72 Resin layer
81 Separation prevention screw (separation prevention member)

The invention claimed is:

1. A weight measurement device comprising:
an upper surface cover on which a measurement target is placed;
a load cell to detect weight of the measurement target placed on the upper surface cover;
a bridge to support the load cell;
a receiving member to receive the weight of the measurement target placed on the upper surface cover; and
a bottom surface cover provided on a lower surface side of the receiving member,
wherein the weight measurement device further comprises a sliding part provided between the lower surface of the receiving member and an upper surface of the bottom surface cover to enable the receiving member to move in a horizontal direction relative to the bottom cover, and
wherein the bridge comprises a pivot which is a fulcrum to make it possible to change inclination of the bridge relative to the bottom surface cover and is in contact with an upper surface of the receiving member.

2. The weight measurement device according to claim 1, wherein friction coefficient of the sliding part is set to satisfy the relationship that when the upper surface cover deflects due to the weight of the measurement target placed on the upper surface cover, friction force generated between the receiving member and the bottom surface cover is smaller than friction force generated between the pivot and the receiving member.

3. The weight measurement device according to claim 2, wherein the sliding part is a sheet made of resin pasted on at least one of the lower surface of the receiving member and the upper surface of the bottom surface cover.

4. The weight measurement device according to claim 3, wherein the sheet made of resin is a sheet made of fluorocarbon resin.

5. The weight measurement device according to claim 2, wherein the sliding part is resin coated on at least one of the lower surface of the receiving member and the upper surface of the bottom surface cover.

6. The weight measurement device according to claim 5, wherein the coated resin is fluorocarbon resin.

7. The weight measurement device according to claim 2, wherein the sliding part is at least one of the lower surface of the receiving member and the upper surface of the bottom surface cover having been subjected to plating treatment.

8. The weight measurement device according to claim 1, wherein the receiving member comprises: a plate-shaped part in contact with the pivot; an elastic part provided on an outer periphery of the plate-shaped part; and an outer frame part provided on an outer periphery of the elastic part,
wherein only the outer frame part is attached to the bottom surface cover without attaching the plate-shaped part and the elastic part to the bottom surface cover.

9. The weight measurement device according to claim 1, further comprising a leaf spring to attach the bridge to the bottom surface cover side,
wherein the leaf spring has a peripheral part fixed to the bottom surface cover, and is formed to be elastically deformable.

10. The weight measurement device according to claim 9, wherein the leaf spring is connected to the upper surface cover side,
wherein the weight measurement device further comprises a separation prevention member to prevent the bottom surface cover from being separated from the upper surface cover by a given distance or more, and
wherein the given distance is a distance to prevent the leaf spring fixed to the bottom surface cover side from being stretched to its limit.

11. The weight measurement device according to claim 1, further comprising a reinforcement cover connected to the upper surface cover,
wherein the reinforcement cover comprises an upper surface cover made of metal, a bottom surface cover made of metal, and a resin layer provided between the upper surface cover made of metal and the bottom surface cover made of metal,
wherein many fine recessed parts are formed in a lower surface of the upper surface cover made of metal and an upper surface of the bottom surface cover made of metal, and
wherein resin of the resin layer is filled into the many fine recessed parts so as to bond the upper surface cover made of metal, the resin layer and the bottom surface cover made of metal.

12. The weight measurement device according to claim 2, wherein the receiving member comprises: a plate-shaped part in contact with the pivot; an elastic part provided on an outer periphery of the plate-shaped part; and an outer frame part provided on an outer periphery of the elastic part,
wherein only the outer frame part is attached to the bottom surface cover without attaching the plate-shaped part and the elastic part to the bottom surface cover.

13. The weight measurement device according to claim 3, wherein the receiving member comprises: a plate-shaped part in contact with the pivot; an elastic part provided on an outer periphery of the plate-shaped part; and an outer frame part provided on an outer periphery of the elastic part,
wherein only the outer frame part is attached to the bottom surface cover without attaching the plate-shaped part and the elastic part to the bottom surface cover.

14. The weight measurement device according to claim 4, wherein the receiving member comprises: a plate-shaped part in contact with the pivot; an elastic part provided on an outer periphery of the plate-shaped part; and an outer frame part provided on an outer periphery of the elastic part,
wherein only the outer frame part is attached to the bottom surface cover without attaching the plate-shaped part and the elastic part to the bottom surface cover.

15. The weight measurement device according to claim 2, further comprising a leaf spring to attach the bridge to the bottom surface cover side,
wherein the leaf spring has a peripheral part fixed to the bottom surface cover, and is formed to be elastically deformable.

16. The weight measurement device according to claim 3, further comprising a leaf spring to attach the bridge to the bottom surface cover side,
wherein the leaf spring has a peripheral part fixed to the bottom surface cover, and is formed to be elastically deformable.

17. The weight measurement device according to claim 4, further comprising a leaf spring to attach the bridge to the bottom surface cover side,
wherein the leaf spring has a peripheral part fixed to the bottom surface cover, and is formed to be elastically deformable.

18. The weight measurement device according to claim 2, further comprising a reinforcement cover connected to the upper surface cover,
wherein the reinforcement cover comprises an upper surface cover made of metal, a bottom surface cover made of metal, and a resin layer provided between the upper surface cover made of metal and the bottom surface cover made of metal,
wherein many fine recessed parts are formed in a lower surface of the upper surface cover made of metal and an upper surface of the bottom surface cover made of metal, and
wherein resin of the resin layer is filled into the many fine recessed parts so as to bond the upper surface cover made of metal, the resin layer and the bottom surface cover made of metal.

19. The weight measurement device according to claim 3, further comprising a reinforcement cover connected to the upper surface cover,
wherein the reinforcement cover comprises an upper surface cover made of metal, a bottom surface cover made of metal, and a resin layer provided between the upper surface cover made of metal and the bottom surface cover made of metal,
wherein many fine recessed parts are formed in a lower surface of the upper surface cover made of metal and an upper surface of the bottom surface cover made of metal, and
wherein resin of the resin layer is filled into the many fine recessed parts so as to bond the upper surface cover made of metal, the resin layer and the bottom surface cover made of metal.

20. The weight measurement device according to claim 4, further comprising a reinforcement cover connected to the upper surface cover,
wherein the reinforcement cover comprises an upper surface cover made of metal, a bottom surface cover made of metal, and a resin layer provided between the upper surface cover made of metal and the bottom surface cover made of metal, wherein many fine recessed parts are formed in a lower surface of the upper surface cover made of metal and an upper surface of the bottom surface cover made of metal, and wherein resin of the resin layer is filled into the many fine recessed parts so as to bond the upper surface cover made of metal, the resin layer and the bottom surface cover made of metal.

* * * * *